US008075899B1

(12) United States Patent
Mannering et al.

(10) Patent No.: US 8,075,899 B1
(45) Date of Patent: Dec. 13, 2011

(54) PEPTIDES OF THE A-CHAIN OF PROINSULIN OR INSULIN

(75) Inventors: Stuart Ian Mannering, Reservoir (AU); Leonard Charles Harrison, St. Kilda West (AU); Anthony Wayne Purcell, Macleod (AU); Nicholas A. Williamson, Woodend (AU)

(73) Assignee: The Walter and Eliza Hall Institute of Medical Research, Parkville, Victoria (AU)

( * ) Notice: Subject to any disclaimer, the term of this patent is extended or adjusted under 35 U.S.C. 154(b) by 585 days.

(21) Appl. No.: 11/572,232

(22) PCT Filed: Jul. 22, 2005

(86) PCT No.: PCT/AU2005/001086
§ 371 (c)(1),
(2), (4) Date: May 22, 2007

(87) PCT Pub. No.: WO2006/007667
PCT Pub. Date: Jan. 26, 2006

(30) Foreign Application Priority Data

Jul. 23, 2004 (AU) ................................ 2004904133

(51) Int. Cl.
*A61K 39/00* (2006.01)
*A61K 39/38* (2006.01)
*A61K 38/00* (2006.01)
*A61K 38/04* (2006.01)
*C07K 5/00* (2006.01)
*C07K 17/00* (2006.01)

(52) U.S. Cl. ...................... 424/185.1; 530/326; 530/327

(58) Field of Classification Search ........................ None
See application file for complete search history.

(56) References Cited

U.S. PATENT DOCUMENTS 5,326,559 A * 7/1994 Miller .......................... 424/85.2

FOREIGN PATENT DOCUMENTS

WO  WO 02/074808 A2 * 9/2002

OTHER PUBLICATIONS

Skylar, J.S., et al Diabetes Care. 2003;28:1068-1076.*
Dong, V.M., et al. Ped. Transplant. 1993;3:181-192.*
Marketletter, Marketletter Pubs. (UK). Sep. 13, 1999.*
Pozzilli, P., et al. Diabetol. 2000;43:1000-1004.*
Goodnow, C.C. The Lancet. 2001;357:2115-2121.*
Mannering, S.I., et al. Cli. Exp. Immunol. 2009;156:226-231.*
Bell, J.J., et al. J. Immunol. 2008;180:1508-1516.*
von Herrath, M. and Nepom, G.T. Nature Immunol. 2009;10(2):129-132.*
Leslie, M. Science. 2009;327:1573.*
van der Worp, H.B., et al. PLoS Med. 2010;7(3):1-8.*
Haller, M.J., et al. Eur. J. Immunol. 2009;39:2054-2058.*
Raju, R. et al. 1997 "T Cell recognition of human pre-proinsulin peptides depends on the polymorphism at HLA DQ locus: A study using HLA DQ8 and DQ6 transgenic mice" *Human Immunol* 58:21-29.
Astill, T.P. et al. 2003 "Promiscuous binding of proinsulin peptides to Type 1 diabetes-permissive and —protective HLA class II molecules" *Diabetologia* 46:496-503.
Chang, S.-G. et al. 2003 "Role of disulfide bonds in the structure and activity of human insulin" *Molecules and Cells* 16:323-330.
Hampl, J. et al. 1991 "Presentation of insulin and insulin A chain peptides to mouse T cells: involvement of cysteine residues" *Molecular Immunology* 28:479-487.
Qiao, Z.-S. et al. 2001 "Putative disulfide-forming pathway of porcine insulin precursor during its refolding in vitro" *Biochemistry* 40:2662-2668.
Sieber, P. et al. 1978 "Synthesis and biological activity of two disulphide bond isomers of human insulin: [A7-A11, A6-B7-Cysteine]- and [A6-A7, A11-B7-Cystine]insulin (human)" *Hoppe-Seyler's Z Physiol Chem* 359:113-123.
Williams, D.B. et al. 1993 "Characterization of the insulin A-chain major immunogenic determinant presented by MHC class II 1-$A^d$ molecules" *J Immunol* 151:3627-3637.
Chang et al., "Novel strategy for identification of candidate cytotoxic T-cell epitopes from human preproinsulin." (2003) Tissue Antigens, 62(5): 408-417.
Hua et al. "A protein caught in a kinetic trap: Structures and stabilities of insulin disulfide isomers." (2002) Biochemistry, 41(50): 14700-14715.
Kent et al., "Expanded T cells from pancreatic lymph nodes of type 1 diabetic subjects recognize an insulin epitope." (2005) Nature, 435(7039): 224-228.
Mannering et al., "The insulin A-chain epitope recognised by human T-cells is post-translationally modified." (2005) J Exp Med. 202(9):1191-7.

* cited by examiner

*Primary Examiner* — Gerald R Ewoldt
(74) *Attorney, Agent, or Firm* — Knobbe Martens Olson & Bear LLP

(57) ABSTRACT

The present invention relates generally to the field of immunotherapy and immunodiagnosis of autoimmune conditions. More particularly, the present invention provides peptides of the A-chain of proinsulin or insulin, which are recognized by or are specific for proinsulin- or insulin-sensitized T-cells. The present invention further contemplates the use of the these agents in therapeutic and diagnostic applications for Type 1 diabetes.

6 Claims, 11 Drawing Sheets

MALWMLLLPLLALLALWGPDPAAA FVNQHLCGSHLVEALYLVCGERGFFYTPKT REAEDLQVGQVELGGGPGAGSLQPLALEGSLQKR GIVEQCCTSICSLYQLENYCN

LEADER 1-24    B-chain 1-30    C-peptide 31-65    A-chain 1-21

PEPTIDES OF THE A-CHAIN OF PROINSULIN OR INSULIN

This application is U.S. National Phase of International Application PCT/AU2005/001086, filed Jul. 22, 2005 designating the U.S. and published in English as WO 2006/007667 on Jan. 26, 2006, which claims priority to Australian Patent Application No. 2004904133 filed Jul. 23, 2004.

BACKGROUND OF THE INVENTION

1. Field of the Invention

The present invention relates generally to the field of immunotherapy and immunodiagnosis of autoimmune conditions. More particularly, the present invention provides agents which are recognized by or are specific for proinsulin- or insulin-sensitized T-cells. The present invention further contemplates the use of these agents in therapeutic and diagnostic applications for Type 1 diabetes.

2. Description of the Prior Art

Bibliographic details of the publications referred to in this specification are also collected at the end of the description.

Reference to any prior art in this specification is not, and should not be taken as, an acknowledgment or any form of suggestion that that prior art forms part of the common general knowledge in any country.

Type 1 diabetes (T1D) is caused by autoimmune destruction of the insulin-producing pancreatic β cell. The onset of clinical diabetes is preceded by the appearance of antibodies to (pro)insulin, glutamic acid decarboxylase (GAD) and tyrosine phosphatase-like insulinoma antigen-2 [IA-2] (Verge, et al., *Diabetes* 47:1857-1866, 1998; Harrison, *Pediatr Diabetes*, 2:71-82, 2001). Serum and T-cell transfer experiments in the non-obese diabetic (NOD) mouse, a spontaneous model of T1D, have shown that T-cells, not antibodies, mediate the destruction of the 13 cells (Kitutani et al., *Adv. Immunol.*, 51:285-322, 1992). Furthermore, CD4+ T-cells are absolutely required for the development of T1D in the NOD mice (Yagi et al., *Eur. J. Immunol.* 22:2387-2393, 1992). Many genetic loci have been associated with risk of T1D, but the highest risk is with the major histocompatibility locus (IDDM 1), in particular with class II HLA genes in humans, specifically the haplotypes HLA-DR3-DQ2 and HLA-DR4-DQ8 (Pugliese et al., *Type 1* diabetes. Molecular, cellular, and clinical immunology: 134-152, 1996; Tait et al., *Hum. Immunol*, 42:116-122, 1995). HLA class II molecules present processed protein antigens in the form of short (>11-amino acids) peptides to CD4+ T-cells, underlining the importance of CD4+ T-cells in the development of T1D.

Proinsulin is the major protein product of the βcell and, with the possible exception of rare self-antigen expressing cells in lymphoid tissues, is the only known human islet autoantigen expressed solely in β cells. An increasing body of evidence implicates autoimmune reactivity to proinsulin as a major mechanism of β cell destruction (Narendran et al., 2004, supra). Autoantibodies to insulin are associated with early onset of disease (Ziegler et al., *Diabetes* 40:709-714, 1991), and interestingly with HLA DR4 (Eisenbarth et al., *J. Autoimmun.*, 5Suppl. A: 241-246, 1992). The second strongest genetic susceptibility locus for T1D, IDDM 2, maps to a variable nucleotide tandem repeat (VNTR) minisatellite upstream of the insulin gene (Lucassen et al., *Nat. Genet*, 4:305-310, 1993). The short class I VNTR (26-63 repeats) alleles are associated with lower levels of proinsulin gene transcription in the thymus and, it is postulated, with less deletion of proinsulin-specific T-cells and an increased risk of developing T1D; in contrast, the long class III (140-210 repeats) alleles are associated with higher proinsulin transcription in the thymus, greater deletion of proinsulin-specific T-cells and a lower risk of T1D (Pugliese et al., *Nat Genet*, 15:293-297, 1997). These findings infer that immune responses to proinsulin are critical for the development of T1D.

The amino acid sequence of human proinsulin is shown in FIG. 1. Proinsulin-derived peptides that stimulate human T-cells have been reported (Narendran et al., *Autoimmun. Rev*, 2:204-210, 2003, Lieberman et al., *Tissue Antigens* 62:359-377, 2003), but knowledge of these T-cell epitopes is fragmentary. Proinsulin-derived T-cell epitopes have been identified in three different ways: (1) by cloning insulin- or proinsulin-specific CD4+ T-cells and analyzing the epitope specificity of these cells in vitro; (2) by using synthetic peptides identical to the sequence of proinsulin to recall T-cell proliferation responses from peripheral blood mononuclear cells (PBMC) in vitro; or (3) by immunizing mice that express transgenic HLA genes, isolating T-cell hybridomas specific for proinsulin and analyzing their specificity in vitro. There are few published reports that describe the cloning of human CD4+ insulin- or proinsulin-specific T-cells (see Table 3). Schloot et al., *J. Autoimmun* 11:169-175, 1998 identified an HLA-DR-restricted epitope in the B-chain of insulin (B:11-27). Semana et al., *J. Autoimmun* 12:259-267, 1999 detected T-cell proliferation in response to C35-50 of proinsulin. A single T-cell clone was isolated that recognized this C-peptide epitope although the responses were weak. The first proinsulin T-cell epitope identified from synthetic peptides was B24-C36, in individuals with islet autoantibodies at risk for T1D (Rudy, et al., *Mal Med*, 1:625-633, 1995). Others have tested human T-cells for their capacity to respond to the B9-23 peptide recognized by CD4+ T-cells in NOD mice (Alleva, et al., *J. Clin. Invest.* 107:173-180, 2001). Responses to this peptide were detected in PBMC from diabetic and pre-diabetic donors, but not healthy controls. ELISpot assays have been used to detect T-cell responses to GAD and proinsulin peptides from healthy and diabetic donors (Ott et al., *J. Clin. Immunol.* 24:327-339, 2004). T-cell responses were detected to an epitope C18-A1 in healthy, diabetic and pre-diabetic donors. Donors who had antibodies to islet autoantigens had responses to B11-C24 and C28-A21; donors who had clinical diabetes had responses to B20-C4 (Durinovic-Bello et al., *J. Autoimmun* 18:55-66, 2002). HLA DRB1*0401 transgenic mice were used to identify an HLA DRB1*0401-restricted proinsulin epitope [C56-64] (Congia et al., *Proc. Natl. Acad. Sci. USA* 95:3833-3838, 1998). Raju et al., *Hum. Immunol* 58:21-29, 1997 found that pre-proinsulin 1-24, the entire leader sequence, and B21-C39 were dominant epitopes after immunization of HLA DQ8 transgenic mice. In similar experiments, HLA DQ6 transgenic mice responded to leader 14-B9 and C60-A5 (Raju et al., 1997, supra). In summary, several T-cell epitopes in proinsulin have been reported, but only two have been identified using T-cell clones, and HLA restriction has only been defined with HLA transgenic mice.

Modifications of amino acids that occur after translation of mRNA into polypeptide are known as post-translational modifications (PTMs). PTMs such as phosphorylation, glycosylation and disulphide bond formation are critical for correct protein folding and function. While T-cells that recognize self-peptide antigens are deleted during development or regulated post-natally, PTMs, particularly if induced by inflammation and/or cellular stress, could create 'neo-antigens' that might trigger T-cell responses to modified self, leading to autoimmune disease (reviewed by Doyle and Mamula, *Trends. Immunol.* 22:443-449, 2001). The paradigm that PTMs create target autoantigens is attactive, but there are few examples of PTMs that create human T-cell epitopes. Coeliac disease, although strictly speaking a food intolerance rather than an autoimmune disease, is the clearest example of a human disease in which a PTM of the target antigen leads to a pathogenic T-cell response (Molberg et al., *Nat. Med.* 4:713-717, 1998; Anderson et al., *Nat. Med.* 6:337-442, 2000). Glutamine (Q) residues in the cereal protein gliadin are deamidated by tissue transglutaminase to glutamic acid (E) residues, which are then recognized by pathogenic T-cells.

There is a need to identify major T-cell epitopes in proinsulin and insulin in order to develop therapeutic and diagnostic agents for T1D.

SUMMARY OF THE INVENTION

The present invention provides immunotherapeutic and immunodiagnostic methods and agents useful for T1 D. The present invention is predicated in part on the identification of a class of proinsulin- or insulin-derived A-chain epitope requiring a PTM in order to be fully reactive to proinsulin or insulin-sensitive T-cells and in particular CD4+ T-cells. The PTM is preferably an intra-chain disulfide bond between two adjacent cysteine residues.

Accordingly, the present invention provides an isolated peptide derivable from the A-chain of proinsulin or insulin and comprising an amino acid sequence having two adjacent cysteine residues which, when both participate in an intra-chain disulfide bond, enables the peptide, to activate proinsulin- or insulin-sensitive CD4+ T-cells or a homolog of said peptide.

The peptide or its homologs, analogs, orthologs, mutants or derivatives represent a T-cell epitope from proinsulin or insulin which requires a PTM in order to be fully reactive with sensitized T-cells. For the sake of brevity, the peptide and its homologs, analogs, orthologs, mutants and derivatives are all encompassed by the term "T-cell reactive agent" or "TCRA".

The present invention contemplates, therefore, methods for diagnosing T1D or a susceptibility for development of same in a subject. The present invention further provides methods of treatment or prophylaxis of a subject with or having a pre-disposition to develop T1D. The present invention also provides diagnostic and therapeutic, including prophylactic, agents to treat or help prevent T1D or at least ameliorate the symptoms of T1D. The present invention further contemplates a method for diagnosing and/or preventing immune T-cell responses that could attack transplanted (pro)insulin-producing cells or tissue.

Vaccines and tolerance-inducing compositions are also provided in the treatment or prevention of T1D. Generally, the vaccines or compositions comprise the TCRAs of the present invention or agents capable of interacting with same.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

TABLE 1

Summary of Sequence Identifiers

| SEQ ID NO: | Description |
|---|---|
| 1 | Amino acid sequence of human pre-proinsulin |
| 2-22 | Human proinsulin epitopes listed in Table 3 |
| 23 | Synthetic human A-chain peptide |
| 24 | Synthetic human S-8 peptide |
| 25 | Synthetic human S-9 peptide |
| 26 | Synthetic human S-13 peptide (subject to PTM) |
| 27 | Synthetic mouse homolog of S-13 |
| 28 | Forward anchor prime for cloning TCR |
| 29 | TCR alphA-chain reverse primer |
| 30 | TCR betA-chain reverse primer |
| 31 | Synthetic mouse proinsulin II amino acids C53-A7 |
| 32 | Synthetic mouse proinsulin II amino acids C64-A13 |
| 33 | Synthetic mouse proinsulin II amino acids C64-A13 (A6,A7, A11 are serine) |
| 34 | T-cell neoepitope from proinsulin (human) |
| 35 | T-cell neoepitope from proinsulin (mouse) |
| 36-54 | Overlapping human proinsulin peptides |
| 55 | Synthetic human proinsulin A-chain epitope with cysteines replaced by alanine |

A list of abbreviations used in the subject specification is provided in Table 2.

TABLE 2

Abbreviations

| Abbreviation | Definition |
|---|---|
| APC | Antigen presenting cells |
| APL | Altered peptide ligand |
| CFSE | 5,6-carboxyfluorescein diacetate succinimidyl ester |
| GAD | Glutamic acid decarboxylase |
| IA-2 | Tyrosine phosphatase-like insulinome antigen |
| IMDM | Iscove's modified Dulbecco's medium |
| NOD | Non-obese diabetic mouse |
| PTM | Post-translational modification |
| PBMC | Peripheral blood mononuclear cells |
| PBS | Phosphate buffered saline |
| TCEP | Tris (2-carboxyethyl) phosphine hydrochloride |
| TCR | T-cell receptor |
| TCRA | T-cell reactive agent |
| T1D | Type 1 diabetes |
| VNTR | Variable nucleotide tandem repeat |

A summary of human proinsulin peptide-containing epitopes is provided in Table 3.

TABLE 3

Summary of human proinsulin eptiopes

| Epitope[#] | Sequence | Method | Ref | SEQ ID NO: |
|---|---|---|---|---|
| B9-23 | SHLVEALYLVCGERG | ELISpot and $^3$H-thymidine | Alleva, et al., J. Clin. Invest. 107:173-180, 2001 | 2 |

TABLE 3-continued

Summary of human proinsulin eptiopes

| Epitope# | Sequence | Method | Ref | SEQ ID NO: |
|---|---|---|---|---|
| B24-C36 | FFYTPKTRREAED | ³H-thymidine | Rudy, et al., *Mol Med*, 1:625-633, 1995 | 3 |
| B14-C37 | ALYLVCGERGFFYTPKTRREAEDL | ³H-thymidine | Narendran et al., *Autoimmun. Rev*, 2:204-210, 2003 | 4 |
| C56-A7 | LALEGSLQKRGIVEQCC | ³H-thymidine | Rudy, et al., *Mol Med*, 1:625-633, 1995 | |
| B11-27 | LVEALYLVCGERGFFYT | ³H-thymidine | Durinovic-Bello et al., *J. Autoimmun* 18:55-66, 2002 | 6 |
| B20-34 | GERGFFYTPKTRREA | ³H-thymidine | Durinovic-Bello et al., *J. Autoimmun* 18:55-66, 2002 | 7 |
| B30-C44 | TPKTRREAEDLQVGQVEL | ³H-thymidine | Durinovic-Bello et al., *J. Autoimmun* 18:55-66, 2002 | 8 |
| C38-054 | QVGQVELGGGPGAGSLQ | ³H-thymidine | Durinovic-Bello et al., *J. Autoimmun* 18:55-66, 2002 | 9 |
| C58-A11 | LEGSLQKRGIVEQCCTSIC | ³H-thymidine | Durinovic-Bello et al., *J. Autoimmun* 18:55-66, 2002 | 10 |
| A7-A21 | CTSICSLYQLENYCN | ³H-thymidine | Durinovic-Bello et al., *J. Autoimmun* 18:55-66, 2002 | 11 |
| B11-B27 | LVEALYLVCGERGFFYT | T-cell clone | Schloot et al., *J. Autoimmun* 11:169-175, 1998 | 12 |
| C35-50 | EDLQVGQVELGGGPGA | T-cell clone | Semana et al., *J. Autoimmun* 12:259-267, 1999 | 13 |
| L1-24 | MALWMRLLPLLALLALWGPDPAAA | HLA DQ8 mouse | Raju et al., *Hum. Immunol* 58:21-29, 1997 | 14 |
| B19-C36 | GERGFFYTPKTRREAEDLQV | HLA DQ8 mouse | Raju et al., *Hum. Immunol* 58:21-29, 1997 | 15 |
| L11-B8 | LALWGPDPAAAFVNQHLCG | HLA DQ6 mouse | Raju et al., *Hum. Immunol* 58:21-29, 1997 | 16 |
| B19-C38 | GERGFFYTPKTRREAEDLQV | HLA DQ6 mouse | Raju et al., *Hum. Immunol* 58:21-29, 1997 | 17 |
| C9-A3 | GSLQPLALEGSLQKRGIVE | HLA DQ6 mouse | Raju et al., *Hum. Immunol* 58:21-29, 1997 | 18 |

TABLE 3-continued

Summary of human proinsulin eptiopes

| Epitope# | Sequence | Method | Ref | SEQ ID NO: |
|---|---|---|---|---|
| L11-B2 | LALLALWGPDPAAAFV | HLA DR4 mouse | Congia et al., Proc. Natl. Acad. Sci USA 95:3833-3838, 1998 | 19 |
| L21-B12 | PAAAFVNQHLCGSHLV | HLA DR4 mouse | Congia et al., Proc. Natl. Acad. Sci USA 95:3833-3838, 1998 | 20 |
| C49-A1 | GAGSLQPLALEGSLQKRG | HLA DR4 mouse | Congia et al., Proc. Natl. Acad. Sci USA 95:3833-3838, 1998 | 21 |
| C61-A12 | SLQKRGIVEQCCTSICS | HLA DR4 mouse | Congia et al., Proc. Natl. Acad. Sci USA 95:3833-3838, 1998 | 22 |

B = insulin B chain;
C = proinsulin connecting (C) peptide;
A = insulin A-chain;
L = proinsulin leader sequence A list of three letter and single letter amino acid abbreviations is provided in Table 4.

TABLE 4

Single and three letter amino acid code

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BRIEF DESCRIPTION OF THE FIGURES

FIG. 1 is a representation of the amino acid sequence of human proinsulin (SEQ ID NO:1).

FIG. 5 is a graphical representation showing that adjacent cysteines are required to stimulate T-cell clones. The effect of substituting each cysteine with serine was investigated. (A) Insulin-specific T-cell clones ($2.5 \times 10^4$ cells/well) were cultured in the presence of 10 to 0.001 μM A-chain epitope or variants that have each cysteine (C) substituted with serine (S). The substituted amino acid is shown in bold type. Similar results were obtained with three other insulin-specific clones. KRGIVEQCCTSICSL, (SEQ ID NO: 23); KRGIVEQSCTSICSL, (SEQ ID NO: 24); DRGIVEQCSTSICSL, (SEQ ID NO: 25); and KRGIVEQCCTSISSL, (SEQ ID NO: 26). (B) In separate experiments, responses to the native sequence (KRGIVEQCCTSICSL; SEQ ID NO: 23) and a more potent variant (S-13, KRGIVEQCCTSISSL; SEQ ID NO:26) were compared to the murine homologue (KRGIVDQCCTSICSL; SEQ ID NO:27).

DETAILED DESCRIPTION OF THE PREFERRED EMBODIMENTS

Figure 2:
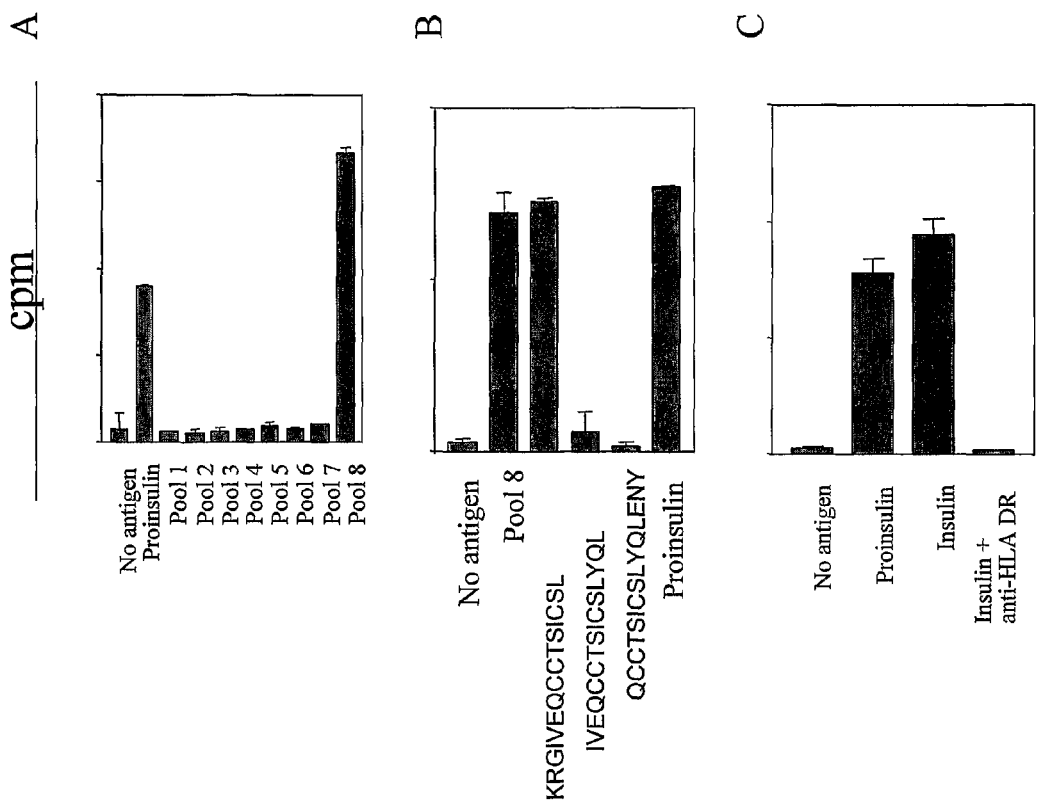
FIG. 2 is a graphical representation showing that the epitope is in the first 12 amino acids of the A-chain of insulin. Proinsulin specific CD4+ T-cell clones were tested against a panel of peptides corresponding to the sequence of human proinsulin. (A) Preliminary epitope mapping. 15mer peptides shifted by three amino acids, comprising the entire sequence of proinsulin, were grouped into 8 pools of 3-4 peptides each. T-cell clones ($5 \times 10^4$ cells/well) were cultured in the presence of irradiated autologous PBMC ($5 \times 10^4$/well) and each peptide pool. Individual peptides were at a final concentration of 5 m/ml and recombinant human proinsulin at 10 m/ml. (B) Fine epitope mapping. The three peptides that comprised pool 8 were tested separately at a final concentration of 5 m/ml. Other conditions were the same as for (A) above. KRGIVEQCCTSICSL, (SEQ ID NO: 23); IVEQCCTSICS-LYQL, (SEQ ID NO: 64); QCCTSICSLYQLENY, (SEQ ID NO: 65). (C) Cloned T-cells were cultured without antigen or with 10 μg/ml proinsulin or 10 m/ml recombinant human insulin. Anti-HLA DR monoclonal antibody (L243) was added to a final concentration of 5 μg/ml. Proliferation (mean of triplicate +/−SD) was measured in all experiments by the addition of 0.5 μCi/well $^3$H-thymidine for the final 18 hours of a 72-hour culture. One representative of five clones is shown.

Before describing the present invention in detail, it is to be understood that unless otherwise indicated, the subject invention is not limited to specific formulations of components, manufacturing methods, dosage or diagnostic regimes, or the like, as such may vary. It is also to be understood that the terminology used herein is for the purpose of describing particular embodiments only, and is not intended to be limiting.

The singular forms "a", "an" and "the" include plural aspects unless the context clearly dictates otherwise. Thus, for example, reference to "a peptide" includes a single peptide, as well as two or more peptides; reference to "a T-cell" includes a single T-cell as well as two or more T-cells; reference to "a TCRA" includes a single TCRA as well as two or more TCRAs and so forth.

In describing and claiming the present invention, the following terminology is used in accordance with the definitions set forth below.

The terms "peptide", "compound", TCRA, "active agent", "chemical agent", "pharmacologically active agent", "medicament", "active" and "drug" are used interchangeably herein to refer to a TCRA that induces a desired pharmacological and/or physiological effect. The term "TCRA" also includes agonists and antagonists of TCRAs.

The terms also encompass pharmaceutically acceptable and pharmacologically active ingredients of those active agents specifically mentioned herein including but not limited to salts, esters, amides, prodrugs, active metabolites, analogs and the like. When the terms "peptide", "compound", TCRA, "active agent", "chemical agent" "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

Reference to a "peptide", "compound", TCRA, "active agent", "chemical agent" "pharmacologically active agent", "medicament", "active" and "drug" includes combinations of two or more actives such as two or more peptides. A "combination" also includes multi-part such as a two-part composition where the agents are provided separately and given or dispensed separately or admixed together prior to dispensation.

For example, a multi-part pharmaceutical pack may have two or more TCRAs maintained separately or a TCRA and an immunosuppressant agent.

The terms "effective amount" and "therapeutically effective amount" of an agent as used herein mean a sufficient amount of the agent (e.g. TCRA) to provide the desired therapeutic or physiological effect or outcome including the desired immunological outcome (e.g. immunological tolerance). Undesirable effects, e.g. side effects, are sometimes manifested along with the desired therapeutic effect; hence, a practitioner balances the potential benefits against the potential risks in determining what is an appropriate "effective amount". The exact amount of agent required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms of T1D, elimination of symptoms and/or underlying cause, prevention of the occurrence of symptoms of T1D and/or their underlying cause and improvement or remediation or amelioration of damage following a T1D.

"Treating" a subject may involve prevention of T1D or other adverse physiological event in a susceptible subject as well as treatment of a clinically symptomatic subject by ameliorating the symptoms of T1D.

A "subject" as used herein refers to an animal, preferably a mammal and more preferably a human who can benefit from the pharmaceutical formulations and methods of the present invention. There is no limitation on the type of animal that could benefit from the presently described pharmaceutical formulations and methods. A subject regardless of whether a human or non-human animal may be referred to as an individual, patient, animal, host or recipient as well as subject. The compounds and methods of the present invention have applications in human medicine, veterinary medicine as well as in general, domestic or wild animal husbandry.

As indicated above, the preferred animals are humans or other primates such as orangutangs, gorillas, marmosets, livestock animals, laboratory test animals, companion animals or captive wild animals.

Examples of laboratory test animals include mice, rats, rabbits, guinea pigs and hamsters. Rabbits and rodent animals, such as rats and mice, provide a convenient test system or animal model. Livestock animals include sheep, cows, pigs, goats, horses and donkeys.

The present invention identifies an epitope in the A-chain of proinsulin or insulin which comprises a T-cell reactive portion to proinsulin- or insulin-sensitized CD4$^+$ T-cells. The epitopes are conveniently on a peptide or a homolog, analog, ortholog, mutant or derivative of the peptide, collectively referred to herein as a T-cell reactive agent or TCRA. The peptides or functional equivalents are, therefore, T-cell epitopes or have the capacity for T-cell epitopes. The present invention provides, therefore, T-cell pre-epitopes which, through PTM form T-cell neoepitopes from proinsulin and insulin.

The "neoepitope" in this context means that it is a newly formed epitope. The neoepitope forms from a pre-epitope. In a preferred embodiment, a PTM transforms a T-cell pre-epitope to an active T-cell neoepitope which is capable of stimulating proinsulin or insulin-sensitized T-cells, and in particular CD4$^+$ T-cells.

In a preferred embodiment, the PTM is the formulation of a disulfide bond between two adjacent cysteine residues. The disulfide bond is, therefore an intra-chain disulfide bond. The present invention extends however, to other PTMs whether naturally occurring or artificially induced.

Accordingly, the present invention provides an isolated peptide comprising at least 10 amino acid residues in length forming a sequence substantially homologous to at least 10 contiguous amino acids within amino acid residues 1 through 21 of the A-chain of human proinsulin or insulin or their mammalian homologs wherein said amino acid sequence comprises two adjacent cysteine residues which when participating in disulfide bond formulation between each other, renders the peptide is capable of stimulating proinsulin- or insulin-sensitized T-cells, or a homolog, analog, ortholog, mutant or derivative of said peptide.

By "substantially homologous" includes the situation where within the homologous amino acid sequence on pro-insulin or insulin, the sequence contains one or more amino acid substitutions, additions or deletions.

The peptide of the present invention is regarded as a T-cell epitope reactive with proinsulin- or insulin-sensitized T-cells and in particular CD4$^+$ T-cells when the two adjacent cysteine residues participate in disulfide bond formulation. Prior to disulfide bond formulation, the peptide (or its functional equivalents) is said to be a T-cell pre-epitope. The peptide and its homologs, analogs, orthologs, mutants and derivatives are referred to as a "TCRA".

The concept of a "T-cell epitope" signifies an antigenic/immunogenic sequence of a protein which brings about an activation of T-cells and comprises in accordance with the present invention the primary sequence of the T-cell epitope or the primary sequence of an (antigenic) polypeptide or protein or antigen which contains at least one primary sequence of a T-cell epitope. T-cells recognize this stimulus normally in the form of a peptide bound to MHC molecules and in particular MHC class II molecules. T-cell epitopes can also bring about only a partial activation in certain instances, in which a decoupling of various processes associated with the T-cell activation can take place. Full or partial activation of T-cells may result in release of mediator substances (e.g. cytokines).

A homolog, analog, ortholog, mutant or derivative of the subject peptide also includes an altered peptide ligand (APL). An APL of the present invention includes a single or multiple amino acid substitution, deletion or addition of an amino acid residue in the peptide or a change in PTM. Changes in PTM include the introduction or removal of particular glycosylation patterns, covalent bonds, ionic bonds, disulfide bonds or the introduction of other groups such as unsaturated or saturated fatty acid moieties or chains.

The present invention provides, therefore, an isolated T-cell neoepitope created by a PTM characterized by:
(i) comprising a peptide backbone of at least 10 amino acids having an amino acid sequence substantially homologous to an amino acid sequence of the A-chain of proinsulin or insulin;
(ii) wherein the amino acid sequence of the peptide comprises at least two adjacent cysteine residues of which at least one corresponds to Cys6 or Cys7 in human proinsulin or insulin A-chain or a non-human mammalian equivalent thereof;
(iii) when functioning as a T-cell epitope for proinsulin- or insulin-sensitized CD4$^+$ T-cells, the two adjacent cysteine residues participate in disulfide bond formulation between each other;
or a homolog, analog, ortholog, mutant or derivative of said peptide.

The preferred T-cell epitope of the present invention comprises the amino acid sequence set forth in SEQ ID NO:26.

However, the present invention extends to a range of fragments of the insulin A-chain which comprise at least two adjacent cysteine residues provided that at least one corresponds to Cys6 or Cys7 although most preferably both Cys6 and Cys7.

For example, the peptide may comprise amino acids 1 through 20, 2 through 20, 3 through 20, 4 through 20, 5 through 20 or 2 through 19, 2 through 18, 2 through 17, 2 through 16, 2 through 15, 2 through 14, 2 through 13, 2 through 12, 2 through 11, 2 through 10, 2 through 9, 2 through 8 or 3 through 19, 3 through 18, 3 through 17, 3 through 16, 3 through 15, 3 through 14, 3 through 13, 3 through 12, 3 through 11, 3 through 10, 3 through 9 or 4 through 19, 4 through 18, 4 through 17, 4 through 16, 4 through 15, 4 through 14, 4 through 13, 4 through 12, 4 through 11, 4 through 10, 4 through 9, 4 through 8 or 5 through 19, 5 through 18, 5 through 17, 5 through 16, 5 through 15, 5 through 14, 5 through 13, 5 through 12, 5 through 11, 5 through 10, 5 through 9, 5 through 8 or 6 through 19, 6 through 18, 6 through 17, 6 through 16, 6 through 15, 6 through 14, 6 through 13, 6 through 12, 6 through 11, 6 through 10, 6 through 9 or 6 through 8 of the A-chain of human proinsulin or insulin or non-human mammalian equivalents or homologs thereof.

As stated above, the peptide defined by SEQ ID NO:26 is most preferred as well as homologs, analogs, orthologs, mutants and derivatives thereof. Reference to the above "TCRAs" include peptides having at least 80% similarity to SEQ ID NO:26 after optimal alignment provided that there are at lest two adjacent cysteine residues of which at least one corresponds to Cys6 or Cys7 of the human A-chain of proinsulin or insulin of its non-human mammalian equivalent. At least 80% includes 80, 81, 82, 83, 84, 85, 86, 87, 88, 89, 90, 91, 92, 93, 94, 95, 96, 97, 98, 99, 100%.

As indicated above, in accordance with the present invention, PTM creates a neoepitope for proinsulin- or insulin-sensitized CD4+ T-cells wherein the PTM is the formulation of a disulfide bond between Cys6 and Cys7. The present invention extends to the introduction of non-naturally occurring amino acid residues to facilitate the same conformational constraints imposed by the disulfide bond between Cys6 and Cys7. Alternatively, the use of non-naturally occurring amino acids can be used to stabilize the peptide for use in in vitro or in vivo diagnostic or therapeutic testing.

An "analog" is generally a chemical analog and include, but are not limited to, modification to side chains, incorporation of unnatural amino acids and/or their derivatives during peptide, polypeptide or protein synthesis and the use of crosslinkers and other methods which impose conformational constraints on the peptides.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 5.

TABLE 5

| Non-conventional amino acid | Code |
| --- | --- |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |

TABLE 5-continued

| Non-conventional amino acid | Code |
|---|---|
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-Nmethylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates chemical analogs of the subject polypeptide capable of acting as antagonists or agonists of the T-cell epitope peptide or other TCRA. Chemical analogs may not necessarily be derived from the instant peptide molecules but may share certain conformational similarities. Alternatively, chemical analogs may be specifically designed to mimic certain physiochemical properties of the subject peptide T-cell epitope. Chemical analogs may be chemically synthesized or may be detected following, for example, natural product screening or screening of chemical libraries. The latter refers to molecules identified from various environmental sources such a river beds, coral, plants, microorganisms and insects.

These types of modifications may be important to stabilize the subject TCRAs if administered to an individual or for use as a diagnostic reagent.

Other derivatives contemplated by the present invention include a range of PTMs such as glycosylation and sulfide bond changes.

The designing of mimetics to a TCRA is a known approach to the development of pharmaceuticals based on a "lead" compound such as the peptide defined by SEQ ID NO:26. This might be desirable where the active peptide compound is difficult or expensive to synthesize or where it is unsuitable for a particular method of administration, e.g. peptides are generally unsuitable active agents for oral compositions as they tend to he quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g. by substituting each residue in turn. Alanine scans of peptides are commonly used to refine such peptide motifs. These parts or residues constituting the active region of the compound are known as its "pharmacophore".

Once the pharmacophore has been found, its structure is modeled according to its physical properties, e.g. stereochemistry, bonding, size and/or charge, using data from a range of sources, e.g. spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the MHC class II molecule or the peptide is determined. This can be especially useful where the MHC molecule and/or peptide change conformation on binding, allowing the model to take account of this in the design of the mimetic. Modeling can be used to generate inhibitors which interact with the linear sequence or a three-dimensional configuration.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, the stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

The goal of rational drug design is to produce structural analogs of biologically active polypeptides of interest or of small molecules with which they interact (e.g. agonists, antagonists, inhibitors or enhancers) in order to fashion drugs which are, for example, more active or stable forms of the polypeptide, or which, e.g. enhance or interfere with the function of a polypeptide in vivo. See, e.g. Hodgson (*BioTechnology* 9: 19-21, 1991). In one approach, one first determines the three-dimensional structure of a protein of interest by x-ray crystallography, by computer modeling or most typically, by a combination of approaches. Useful information regarding the structure of a polypeptide may also be gained by modeling based on the structure of homologous proteins. An example of rational drug design is the development of HIV protease inhibitors (Erickson et al., *Science* 249: 527-533, 1990). In addition, target molecules may be analyzed by an alanine scan (Wells, *Methods Enzymol.* 202: 2699-2705, 1991). In this technique, an amino acid residue is replaced by Ala and its effect on the peptide's activity is determined. Each of the amino acid residues of the peptide is analyzed in this manner to determine the important regions of the peptide.

It is also possible to isolate a peptide-specific antibody, selected by a functional assay and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Two-hybrid screening is also useful in identifying other members of a biochemical or genetic pathway associated with a target. Two-hybrid screening conveniently uses *Saccharomyces cerevisiae* and *Saccharomyces pombe*. Target interactions and screens for inhibitors can be carried out using the yeast two-hybrid system, which takes advantage of transcriptional factors that are composed of two physically separable, functional domains. The most commonly used is the yeast GAL4 transcriptional activator consisting of a DNA binding domain and a transcriptional activation domain. Two different cloning vectors are used to generate separate fusions of the GAL4 domains to genes encoding potential binding proteins. The fusion proteins are co-expressed, targeted to the nucleus and if interactions occur, activation of a reporter gene (e.g. lacZ) produces a detectable phenotype. In the present case, for example, *S. cerevisiae* is co-transformed with a library or vector expressing a cDNA GAL4 activation domain fusion and a vector expressing a holocyclotxin-GAL4 binding domain fusion. If lacZ is used as the reporter gene, co-expression of the fusion proteins will produce a blue color. Small molecules or other candidate compounds which interact with a target will result in loss of colour of the cells. Reference may be made to the yeast two-hybrid systems as disclosed by Munder et al. (*Appl. Microbial. Biotechnol.* 52:311-320, 1999) and Young et al (*Nat. Biotechnol.* 16: 946-950, 1998). Molecules thus identified by this system are then re-tested in animal cells.

Another technique for drug screening provides high throughput screening for compounds having suitable binding affinity to a target and is described in detail in Geysen (International Patent Publication No. WO84/03564). Briefly stated, large numbers of different small peptide test compounds are synthesized on a solid substrate, such as plastic pins or some other surface. The peptide test compounds are reacted with a target and washed. Bound target molecule is then detected by methods well known in the art. This method may be adapted for screening for non-peptide, chemical entities. This aspect, therefore, extends to combinatorial approaches to screening for target antagonists or agonists.

Purified target can be coated directly onto plates for use in the aforementioned drug screening techniques. However, non-neutralizing antibodies to the target may also be used to immobilize the target on the solid phase.

The present invention also contemplates the use of competitive drug screening assays in which neutralizing antibodies capable of specifically binding the target compete with a test compound for binding to the target or fragments thereof. In this manner, the antibodies can be used to detect the presence of any peptide which shares one or more antigenic determinants of the target.

As stated above TCRAs have a range of diagnostic and therapeutic utilities.

Any number of methods may be employed to detect T-cells sensitized to the subject T-cell epitope. Immunological testing is one particular method screening for T-cells 'restricted' by particular MHC class II molecules. Accordingly, the present invention extends to antibodies and other immunological agents directed to or preferably specific for the T-cell epitope or the disulfide bond or its binding MHC class II molecule. The antibodies may be monoclonal or polyclonal or may comprise Fab fragments or synthetic forms.

Specific antibodies can be used to screen for the subject T-cell epitope and its fragments. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies referred to above. Both the first and second antibodies may be used in detection assays or a first antibody may be used with a commercially available anti-immunoglobulin antibody. An antibody as contemplated herein includes any antibody specific to any region of the peptide at or near the T-cell epitope.

Both polyclonal and monoclonal antibodies are obtainable by immunization with the subject peptide or larger forms such as an A-chain or a complex between an MHC class II molecule and the peptide and either type is utilizable for immunoassays. The methods of obtaining both types of antibodies are well known in the art. Polyclonal sera are less preferred but are relatively easily prepared by injection of a suitable laboratory animal with an effective amount of subject polypeptide, or antigenic parts thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The presence of the instant T-cell epitope may be detected in a number of ways such as by Western blotting and ELISA procedures. A wide range of immunoassay techniques are available as can be seen by reference to U.S. Pat. Nos. 4,016,043, 4,424,279 and 4,018,653.

The T-cell epitope of the present invention and its neoepitope has a range of uses in therapy.

For example, the TCRA may be used in therapy to induce immunological tolerance. This may be achieved in various ways including administering the peptide by a tolerogenic route (eg via mucosae) or in a tolerogenic form (eg via immature dendritic cells), exposing the thymus to the peptide, using the peptide to induce deletional tolerance such as by stimulating apoptosis in T-cells or by linking a cytotoxic moiety to the peptide or to induce T-cell anergy. The TCRA may also be used to generate antibodies or other immunoreactive molecules specific to the TCRA.

Accordingly, another aspect of the present invention contemplates a method for preventing or reducing the risk of onset of T1D in a subject said method comprising introducing into said subject a T-cell tolerance-inducing effective amount of a peptide having the characteristics of (i) comprising a peptide backbone of at least 10 amino acids having an amino acid sequence substantially homologous to an amino acid sequence of the A-chain of proinsulin or insulin;

(ii) wherein the amino acid sequence of the pepT1De comprises at least two adjacent cysteine residues of which at least one corresponds to Cys6 or Cys7 in human proinsulin or insulin A-chain or a non-human mammalian equivalent thereof;

(iii) when functioning as a T-cell epitope for proinsulin- or insulin-sensitized $CD4^+$ T-cells, the two adjacent cysteine residues participate in disulfide bond formulation between each other; or a homolog, analog, ortholog, mutant or derivative of said peptide.

In an alternative method, the peptide is used to induce selective depletion of proinsulin- or insulin-sensitized $CD4^+$ T-cells. In this regard, the T-cell epitope peptide or other TCRA of the present invention and its neoepitopic form is fused or otherwise associated with a cytotoxic molecule including an apoptotic molecule or radioactive isotope.

In still a further alternative, catalytic antibodies are generated which specifically target the disulfide bond. In this regard, although not wishing to limit the invention to any one hypothesis, it is conceivable that the disulfide bond formed between two adjacent existing residues results in a formation of substantial bend in the protein backbone. The omega torsion angle for such a bend may range from 180 degrees to negative 130 degrees. The result of this bending of the peptide backbone is the possibility of generating an antibody such as a catalytic antibody which is specific for that conformation.

Accordingly, another aspect of the present invention provides a peptide:

(i) comprising a peptide backbone of at least 10 amino acids having an amino acid sequence substantially homologous to an amino acid sequence of the A-chain of proinsulin or insulin;

(ii) wherein the amino acid sequence of the peptide comprises at least two adjacent cysteine residues of which at least one corresponds to Cys6 or Cys7 in human proinsulin or insulin A-chain or a non-human mammalian equivalent thereof;

(iii) when functioning as a T-cell epitope for proinsulin- or insulin-sensitized $CD4^+$ T-cells, the two adjacent cysteine residues participate in disulfide bond formulation between each other;

or a homolog, analog, ortholog, mutant or derivative of said peptide;

wherein said peptide is fused or otherwise bound or associated with a cytotoxic moiety.

Such a peptide is referred to herein as a cytotoxic T-cell targeting agent but is also encompassed by the term TCRA.

Accordingly, another aspect of the present invention provides a method for treating a subject with T1D or a predisposition for the development of same said method comprising administration to said subject of a peptide which is an amount sufficient to be cytotoxic to $CD4^+$ T-cells wherein in said peptides is characterized by:

(i) comprising a peptide backbone of at least 10 amino acids having an amino acid sequence substantially homologous to an amino acid sequence of the A-chain of proinsulin or insulin;

(ii) wherein the amino acid sequence of the peptide comprises at least two adjacent cysteine residues of which at least one corresponds to Cys6 or Cys7 in human proinsulin or insulin A-chain or a non-human mammalian equivalent thereof;

(iii) when functioning as a T-cell epitope for proinsulin- or insulin-sensitized CD4+ T-cells, the two adjacent cysteine residues participate in disulfide bond formulation between each other;

or a homolog, analog, ortholog, mutant or derivative of said peptide.

The present invention further contemplates a method for diagnosing and/or preventing immune T-cell responses that could attack transplanted (pro)insulin-producing cells or tissue.

In another aspect, the present invention contemplates MHC class II molecules are loaded with peptides comprising the subject T-cell epitope. The peptides are typically loaded into the binding groove formed by the alpha and beta.1 domains and bind to the MHC class II molecules through non-covalent interactions. The peptides can be from about 9 to 10 to about 20 amino acids, or more, in length.

The peptides of the present invention are conveniently synthetically produced but the sequence is derived from pro-insulin or insulin.

The peptides can be prepared in a variety of ways. For example, peptides can be synthesized using an automated peptide synthesizer. The peptides can also be manually synthesized (Haunkapiller et al, *Nature* 310:105-11, 1984, Stewart and Young, *Solid Phase Peptide Synthesis, 2nd Ed*., Pierce Chemical Co., Rockford III, 1984, Houben-Weyl, *Methoden der organischen Chemie*. Vol. 15/1 and 15/2, Bodanszky, *Principles of Peptide Synthesis*, Springer Verlag 1984). alternatively, peptides can be synthesized by proteolytic cleavage (e.g. by trypsin, chymotrypsin, papain, V8 protease, and the like) or specific chemical cleavage (e.g. cyanogen bromide). The peptides can also be synthesized by expression of overlapping nucleic acid sequences in vivo or in vitro, each nucleic acid sequence encoding a particular peptide.

The peptides optionally can be isolated and purified prior to contacting with the MHC class II molecules. Suitable methods include, for example, chromatography (e.g. ion exchange chromatography, affinity chromatography, sizing column chromatography, high pressure liquid chromatography, and the like), centrifugation, differential solubility, or by any other suitable technique for the purification of peptides or proteins. In certain embodiments, the peptides can be labeled (e.g with a radioactive label, a luminescent label, an affinity tag, and the like) to facilitate purification of the peptides (infra).

The peptides are typically not cross-linked to the MHC class II molecules. In other embodiments, the peptides optionally can be cross-linked to the binding groove of the MHC class II molecules. For example, bi-functional crosslinking reagents (e.g. hetero-bifunctional, homo-bi-functional, etc.) can be used to covalently link the peptides to the MHC class II molecules (Kunkel et al., *Mol. Cell. Biochem*. 34:3, 1981). Suitable crosslinking reagents include, for example, dimethylsuberimidate, glutaraldehyde, succinim-idyloxycarbonyl.alpha.-methyl.alpha.(2-pyridyldithio)-toluene (SMTP), N-succinimidyl 3-(2-pyridyldithio_-propionate (SPDP), sulfosuccinimidyl 4-(N-maleimidomethyl)cyclohexane-1-carboxylate (sulfo-SMCC), m-maleimidobenzoyl-N-hydroxysuccinimide ester (MBS), m-maleimidobenzoyl-N-hydroxysulfosuccinimide ester (sulfo-MBS), N-succinimidyl(4-iodoacetyl)aminobenzoate (SIAB), N-sulfosuccinimidyl(4-1-odoacetyl)aminobenzoate (sulfo-SIAB), succinimidyl-4-(p-maleimidophenyl)bu-tyrate (SMPB), sulfosuccinimidyl-4-(p-maleimidophyenyl butyrate (sulfo-SMPB), 1-ethyl-3-(3-dimethylaminopropylcarbodiimide hydrochloride (EDC), dithiobissuccinimidylpropionate (DSP), 3,3' dithiobis(sulfosuccinim-idylpropionate) (DTSSP) and the like (Pierce Chemical Co. *Pierce Immuno Technology Catalog and Handbook,* 1990). In one embodiment, one or more anchor residues of a peptide can be cross-linked to the MHC class II molecule. In other embodiments, any suitable residue(s) of a peptide can be cross-linked to the MHC class II molecule.

Alternatively, the peptides can be prepared as fusion proteins with a soluble MHC class II.beta. subunit. For example, nucleic acids encoding a peptide, or a mixture of peptides, can be expressed as a fusion protein comprising a peptide, spacer or linker region (e.g 10 to 20 amino acid linker), a soluble MHC class II subunit, and a ligand binding domain. The peptide can be linked for example, to the amino terminal end of the MHC class II.beta. subunit. In one embodiment, the fusion protein is expressed from an expression cassette. The expression cassette can included, for example, a promoter operably associated with, and in a 5' to 3' direction relative to the direction of transcription, a nucleic acid encoding a polylinker cloning region, a nucleic acid encoding a spacer region, and a nucleic acid encoding an MHC class II.beta. subunit. The expression cassette can be expressed in any suitable host organism and can be part of an expression vector. In another embodiment, pools of MHC class II/peptide fusion protein pairs can be prepared by inserting degenerate, semi-degenerate or non-degenerate nucleic acids into the polylinker region of an expression cassette, such as those described above. Alternatively, nucleic acids encoding a single peptide can be inserted into the polylinker region.

The MHC class II molecules and peptides can be formed into multimeric MHC class II complexes. As used herein, forming multimeric MHC class II/peptide complexes can include forming multimeric MHC class II/peptide complexes from MHC class II molecule/peptide pairs and/or forming multimeric MHC class II molecules from MHC class II molecules, which can be loaded with peptides.

The multimeric complexes can comprise two, three, four, or more MHC class II/peptide complexes. Such complexes can be formed by interaction between a ligand on the MHC class II molecules and a polyvalent binding partner. As used herein, the phrase "ligand-ligand binding partner pair" refers to a ligand and its ligand binding partner that are capable of recognizing and binding to each other. The term "polyvalent" refers to a ligand binding partner that has at least two binding sites, typically three or four, ligand binding sites. The ligand(s) and binding partner can be any moieties that are capable of reconginzing and binding to each other to form a multimeric complex. Additionally, the ligand and binding partner can interact via the binding of a third intermediary substance. Typically, the ligand and ligand-binding partner constituting the ligand-binding partner pair are binding molecules that undergo a specific non-covalent interaction with each other. The ligand and ligand binding partner can be naturally occurring or artificially produced, and optionally can be aggregated with other species of molecules.

The binding partner can be free in solution or can be attached to a solid support. Examples of suitable solid supports include beads (e.g. magnetic beads), membranes, mcirotiter plates, and the like. The support can be glass, plastic (e.g. polystyrene), polysaccharide, nylon, nitrocellulose, PVDF, and the like. The use of a binding partner linked to a solid support can be useful for immobilization and/or isolation of T-cells (e.g. such as from a population of PBMC) that recognize the multimeric MHC class II molecule and the bound peptide.

In an exemplary embodiment, one of the MHC class II subunits includes a modification site (e.g. a BirA recognition sequence); BirA catalyzes biotinylation of the protein substrate. The biotinylated MHC class II molecule is then bound to a polyvalent binding partner (e.g. streptavidin or avidin), to which biotin binds with extremely high affinity. The multimers can then be stored until needed.

The MHC class II molecules typically are loaded with peptide by incubation at 37.degree.C. in a phosphate buffer at slightly acidic pH (.e.g 100 mM sodium phosphate, pH 6.0) in the presence of 0.2% n-octyl-D-glucopyranoisde (OG). A protease inhibitor is optionally added to the mixture. Suitable peptide loading times range from about 48 to about 72 hours, although greater and lesser times are within the scope of the present invention. Suitable peptide: MHC class molecule molar ratios are in excess of 10:1, although greater and lesser ratios are within the scope of the present invention. Other buffers and pHs can be used, as will be appreciated by the skilled artisan.

In certain embodiments, the multimeric MHC class II/peptide complexes are labeled. As used herein, the terms "label" or "labeled" refer to a molecule or groups of molecules which can provide a detectable signal when the label is incorporated into, or attached to, a polypeptide, such as a MHC class II molecule or a polyvalent binding partner. For example, a polypeptide or a polyvalent binding partner can be labeled with a radioactive molecule, a luminescent molecule, a fluorescent molecule, a chemiluminescent molecule, an enzyme, or by biotinyl moieties. Methods of labeling polypeptides and binding partners are well known in the art. Examples of detectable labels include, but are not limited to, the following: radioisotopes (e.g. $^3$H, $^{14}$C, $^{32}$P, $^{35}$s, $^{125}$I, $^{131}$I, and the like), fluorescent molecules (e.g. fluorescein isothiocyanate (FITC), rhodamine, phycoerythrin (PE), phycocyanin, allophycocyanin, ortho-phthaldehyde, fluorescamine, peridinin-chlorophyll a (PerCP), Cy3 (indocarbocyanine), Cy5 (indodiacarbocyanine), lanthanide phosphors, and the like), enzymes (e.g. horseradish peroxidase, .beta.-galactosidase, luciferase, alkaline phosphatase), biotinyl groups, and the like. In some embodiments, detectable labels are attached by spacer arms of various lengths to reduce potential steric hindrance.

In specific embodiments, the binding partner can be labeled. For example, a biotinylated MHC class II molecule can be detected with labeled avidin or streptavidin (e.g streptavidin containing a fluorescent molecule or a colored molecule produced by enzymatic activity that can be detected by optical or colorimetric methods). Alternatively, the MHC class II molecule can be detected, for example, with a labeled antibody or other binding agent that will bind specifically bind to the multimeric MHC class II complex. Suitable labels include any of those described above or known to the skilled artisan.

In another aspect, the multimeric MHC class II/peptide complexes are contacted with T-cells to determine whether the complexes bind the T-cells in an epitope-specific manner. In certain embodiments, the multimeric MHC class II/peptide complexes can be used to stain or detectably label the T-cells. As used herein, "stain" refers to the ability of the multimeric MHC class II/peptide complexes to detectably label T-cells that can bind the complexes in an epitope-specific manner.

Human T-cells can be isolated from fresh samples from a human subject, from an in vitro culture of cells from a human subject, from a frozen sample of cells, and the like. Suitable samples can include, for example, blood, lymph, lymph nodes, spleen, liver, kidney, pancreas, tonsil, thymus, joints, synovia, and other tissues from which T-cells can be isolated. Typically, the T-cells are isolated as peripheral blood mononuclear cells (PBMC). PBMC can be partially purified, for example, by centrifugation (e.g from a buffy coat), by density gradient centrifugation (e.g. through a Ficoll-Hypaque), by panning, affinity separation, cell sorting (e.g. using antibodies specific for one or more cell surface markers) and other techniques that provide enrichment of PBMC and/or T-cells.

In one exemplary embodiment, PBMC are isolated from a blood sample by standard Ficoll-Hypaque method. The blood sample is treated with heparin and underlain with a Ficoll solution. Following centrifugation, the recovered cells can be washed, for example, in PBS or T-cell culture medium (e.g. RPMI 1640 supplemented with 2 mL L-glutamine, 100 .mu.g/ml penicillin/streptomycin, 1 mM sodium pyruvate and 15% pooled human serum; AIM-V; and the like). The washed cells can be resuspended in T-cell culture medium, and the like.

The multimeric class II/peptide complexes can be contacted with the T-cells to identify one or more MHC class II epitopes of a predetermined antigen. The epitopes can be determined according to the specificity of the alpha and beta. subunits comprising the MHC class II molecules.

Generally, the multimeric class II/peptide complexes are contacted with a sample of T-cells of interest. In some embodiments, the T-cells are cultured for between about 1 to 10 days, or more, in T-cell culture media in the presence of the predetermined antigen to stimulate proliferation of T-cells that are specific for that antigen. The media optionally can be supplemented other components for the culture and/or viability of T-cells (e.g. serum, antibiotics, cytokines, co-stimulatory receptor agonists, and the like). In other embodiments, the T-cells are contacted with the multimeric class II/peptide complexes without antigen stimulation and/or culturing (e.g. for patient monitoring).

The T-cells are contacted with the multimeric MHC class II/peptide pools under suitable binding conditions. In one embodiment, the binding conditions are 37.degree.C. in any suitable T-cell culture media (e.g. RPMI 1640 or AIM-V), phosphate buffered saline, Dulbecco's phosphate buffered saline, Dulbecco's Modified Eagle Medium, Iscove's medium, and the like. The media can be supplemented with other components for the culture and/or viability of T-cells (e.g. serum, antibiotics, cytokines, and the like). The multimeric complexes are typically contacted with the T-cells for at least about 5 minutes and typically within the range of about 1 to 2 hours. The appropriate concentration of multimeric complexes can be determined by titration.

The amount of multimeric complex bound to the T-cells is determined. For example, if the T-cells are substantially homogenous, then the amount of labeled multimeric.

Still another aspect of the present invention provides a method for inducing tolerance or anergy. This may be achieved in a number of ways including providing MHC class II/T-cell epitope complexes, introduction of the T-cell epitopes into the thymus, providing sub-optimal levels of the T-cell epitope and providing antagonists of T-cell eptiope-TCR interaction. Examples of suitable antagonists are antibodies or recombinant forms or chimeric forms or derivatives thereof.

The T-cell epitope peptides or their homologs, analogs, orthologs, mutants and derivatives (i.e. the TCRAs) or antibodies, MHC class II complexes or T-cell receptor-TCR antagonist (also referred to herein as "active compounds") used in the methods of the invention can be incorporated into pharmaceutical compositions suitable for administration to a subject, e.g. a human. Such compositions typically also comprise a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g. intravenous, intradermal, subcutaneous, oral (e.g. inhalation), transdermal (topical), transmucosal, and rectal administration. Solution or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl paprabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatis water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the active compound (e.g. a small molecule, nucleic acid molecule, or peptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administrating by inhalation, the compounds are delivered in the form of an aerosol spray from pressured container or dispenser that contains a suitable propellant, e.g. a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (.e.g with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhdrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The present invention is further described by the following non-limiting examples.

EXAMPLE 1

Blood Donors and PBMC Isolation

Blood was obtained by venepuncture. The HLA type of the donors is shown in Table 6. PBMC were isolated over Ficoll/Hypaque (Amersham Pharmacia Biotech AB, Uppsala Sweden) and washed twice in PBS. Cells were cultured in Iscove's modified Dulbecco's medium (IMDM) (Gibco, Rockville, Mass., USA) supplemented with 5% v/v pooled male human serum, 2 mM glutamine (Glutamax, Gibco, Rockville, Mass., USA), $5 \times 10^{-5}$M 2-mercaptoethanol (Sigma, St Louis, Mo.), penicillin (100 U/ml), streptomycin (100 µg/ml) (Gibco, Rockville, Mass., USA) and 100 µM non-essential amino acids (Gibco, Rockville, Mass., USA). Islets and spleen samples were obtained from the Tom Mandel Memorial Islet Transplantation Program, St Vincent's Institute, Melbourne, Australia. Islets were isolated by ductal perfusion with collagenase, digestion and gradient centrifugation as described (Shapiro et al., *N Engl. J. Med.* 343:230-238, 2000).

TABLE 6

Clinical details of blood donors

| Donor | Clinical status | HLA DR | HLA DQ |
|---|---|---|---|
| 1 | Type 1 diabetes | B1*0301, 0404 | B1*0201, 0302 |
| 2 | Pre-clinical Type 1 diabetes | B1*0301, 0404 | B1*0201, 0302 |

EXAMPLE 2

Antigens

Peptides used in this study are shown in Table 7. Recombinant human proinsulin was produced by modification of a published protocol (Cowley and Mackin, *FEBS Lett* 402:124-130, 1997). Briefly, after anion exchange chromatography, refolding and reversed phase HPLC purification, the protein resolved as a single species of correct molecular weight in matrix assisted laser desorption/ionisation—time of flight mass spectrometry. The endotoxin concentration of proinsulin stock measured by *Limulus* lysate assay (BioWhittaker, Walkerville, Md.), was 0.51 EU/mg/ml. Synthetic peptides were purchased from Mimotopes (Clayton, Victoria, Australia) or Auspep (Parkville, Victoria, Australia) and reconstituted to 5 mM in 0.5% v/v acetic acid, 40% v/v acetonitrile—water, aliquoted and stored at −70° C. Clinical grade recombinant human insulin was HUMULIN (Novo, Nordisk, Copenhagen, Denmark). Human islet-cell lysate was prepared from 100 hand-picked islets that were resuspended in 0.5 ml of serum free IMDM then frozen, thawed and sonicated three times. Spleen lysate from the same donor was prepared in a similar manner.

TABLE 7

Peptides used in this study

| Sequence | Name | SEQ ID NO: |
|---|---|---|
| KRGIVEQCCTSICSL | A-chain peptide | 23 |
| KRGIVEQSCTSICSL | S-8 | 24 |
| KRGIVEQCSTSICSL | S-9 | 25 |
| KRGIVEQCCTSISSL | S-13 | 26 |
| KRGIVDQCCTSICSL | Murine homologue | 27 |

EXAMPLE 3

CFSE Staining and T-Cell Cloning

For staining with the dye 5,6-carboxylfluorescein diacetate succinimidyl ester (CFSE) (Molecular Probes, Eugene, Or) PBMC at $1 \times 10^7$/ml in PBS were incubated at 37° C. for 5 minutes with the concentrations of CFSE indicated in the Brief Description of the Figures. Staining was terminated by adding culture medium containing 5% pooled human serum, the cells washed once in PBS/1% pooled human serum and resuspended in culture medium at $2 \times 10^6$/ml. Stained cells ($2 \times 10^5$/well, 100 µl) were cultured in 96-well round bottom plates (Becton Dickinson Labware, Franklin Lakes, N.J., USA) with medium alone or with tetanus toxoid or proinsulin. Unstained cells were included in all experiments and were used to set the compensations on the flow cytometer.

After 7-10 days of culture, cells for each antigen concentration were pooled, washed in PBS and stained on ice with anti-human CD4-PE (IgG2a, clone RPA-T4), (BD Pharmingen, San Diego, Calif.). Optimal compensation and gain settings were determined for each experiment based on unstained and single stained samples. Propidium iodide was used to exclude dead cells. A single $CFSE^{dim}$, $CD4^+$, propidium iodide-negative cell was sorted into all wells, except the outer wells, of a 96-well tray. Each well contained $1 \times 10^5$ freshly prepared, irradiated (20 Gy), allogeneic PBMC from two unrelated donors and $5 \times 10^4$, irradiated (50 Gy) JY Epstein Barr Virus transformed B cell line (EBV), IL-2 (10 U/ml), IL-4 (5 ng/ml) and phytohaemagluttinin (PHA) (2.5 µg/ml), to a final volume of 100 µl. Fresh IL-2 and IL-4 was added after 7 and 14 days of culture. Growing clones were visible after 2-3 weeks and transferred to a 48-well plate, fed with cytokines and screened for antigen specificity. For screening, cells were cultured with autologous irradiated PBMC with or without proinsulin and proliferation was measured by $^3$H-thymidine incorporation as described in Example 4.

EXAMPLE 4

Proliferation Assays

All assays were performed in 96-well round bottom plates in 5% PHS/IMDM. Antigen presenting cells (APC) were either (i) irradiated (20Gy) autologous or HLA-matched PBMC (fresh or thawed), (ii) HLA-typed EBV transformed B lines from the $9^{th}$ International HLA Typing Workshop or (iii) EBV-transformed B cell lines (from a donor with Bare Lymphocyte Syndrome), transfected with different HLA genes. EBV lines were irradiated at 50 Gy. In some experiments APC were fixed with 1% v/v paraformaldehyde for 20 minutes at room temp, washed twice in PBS and once in culture medium before use in proliferation assays.

EXAMPLE 5

Cloning and Sequencing TCR Genes

Total RNA was isolated from $1-5\times10^6$ cloned insulin-specific T-cells with RNAeasy columns (Qiagen, Md., USA). First strand synthesis was carried out with oligo (dT) primers and MMLV reverse transcriptase (Promega, Wis., USA). cDNA was purified using silica and a 5' poly-G anchor was added with terminal transferase (Promega, Wis., USA). TCR genes were amplified with a forward anchor primer (cac tcg agc ggc ccc ccc ccc ccc cc; SEQ ID NO: 28) and either alphA-chain (cag caa cgt ctc tgt ctc tg; SEQ ID NO:29) or beta-chain (gct cta gcg tcg acg gct gct cag gca gta tct gga; SEQ ID NO:30) reverse primers. PCR products were purified, cloned into pGEM and sequenced by Big Dye. Several clones were sequenced in each direction for each clone.

EXAMPLE 6

HPLC Fractionation and Mass Spectrometry

An aliquot of 1.8 mg of peptide was added to 1.8 ml of serum for 1 hr and incubated at 37° C. The mixture was then fractionated by RP-HPLC using an AKTA Basic HPLC (Amersham Biosciences) equipped with a multi wavelength tuneable UV detector and a Frac 950 fraction collector. Proteins were separated on a 300 Å, 4.6×250 mm Vydac protein and peptide C18 column, using a linear gradient of buffer A (0.1% v/v TFA) to 60% v/v B (acetonitrile/0.09% v/v TFA; 0.86%/min), at a flow rate of 1 ml/min. Fractions (500 µl) were collected and 1 µl aliquots were mixed with 1 µl of 2,5-dihydroxybenzoic acid (Agilent) and dried onto a sample stage for analysis by MALDI-QTOF mass spectrometry (Applied Biosystems QSTAR pulsar i). Selected ions were subject to further MSMS analysis. Fragment ions generated in this way were manually assigned based on the known sequence of the parental peptide and modified amino acid residues identified within the sequence.

EXAMPLE 7

Identification of Proinsulin A-Chain Epitope

Fifteen proinsulin-specific CD4+ T-cell clones were isolated from the peripheral blood of a donor with established T1D, as described in Example 1. The epitope was mapped against an overlapping panel of 15-mer peptides, each shifted by three amino acids. First, the clones were each incubated with 8 pools of peptides, each comprising 3-4 peptides. Five of 15 clones recognized a peptide within pool 8 (FIG. 2A). The remaining clones failed to respond to any peptide. Second, when the three peptides in pool 8 were tested separately, a peptide comprising the last two amino acids of the C-peptide (underlined) and the first 13 amino acids of the A-chain of insulin (KRGIVEQCCTSICSL; SEQ ID NO:23) stimulated the clones as well as pool 8 or recombinant proinsulin (FIG. 2B). The epitope is within the A-chain of insulin as clinical grade insulin was able to stimulate the clones. The epitope was confirmed to be within the first 12 amino acids of the A-chain of insulin using a panel of peptides. Finally, the response to insulin was due to antigen-specific recognition since it was blocked by anti-HLA DR specific mAb (FIG. 2C).

EXAMPLE 8

T-Cell Clones to the A-Chain Epitope Recognize Native Insulin

Figure 3:
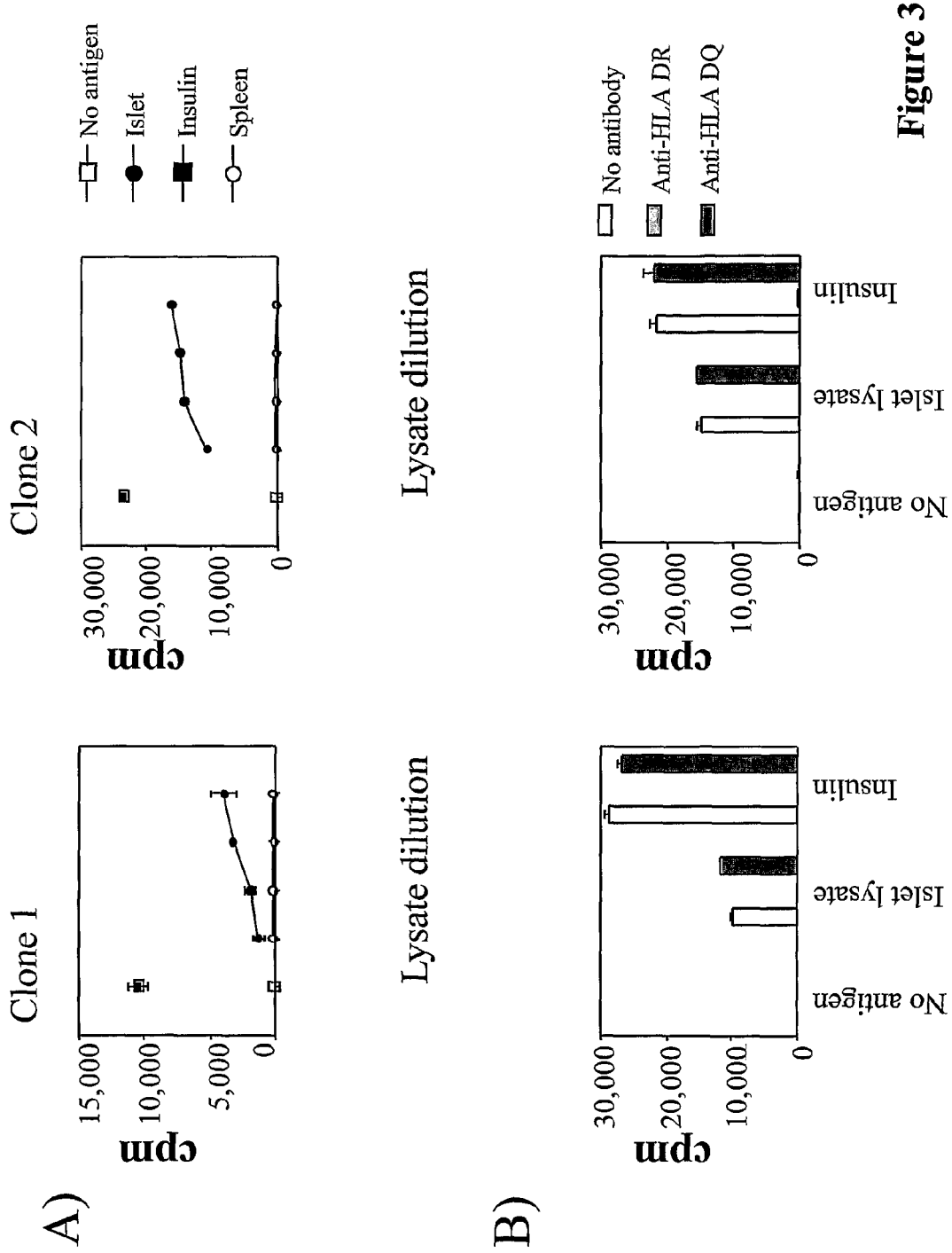
FIG. 3 is a graphical representation showing that T-cell clones recognize native insulin. (A) Insulin-specific T-cell clones were cultured in dilutions of a freeze-thaw lysate of hand-picked human islets or human spleen. Insulin (10 μg/ml) and cells in the absence of antigen served as positive and negative controls, respectively. Similar results were obtained with two other insulin-specific clones. (B) Insulin-specific T-cell clones were cultured without antigen or with 1/400 dilution of islet lysate or 10 m/ml of insulin. Anti-HLA DR (L243, IgG2a) or anti-HLA DQ (SPV-L3, IgG2a) were included at a final concentration of 5 μg/ml.

To confirm that the T-cell clones recognize an epitope derived from native human insulin, their capacity to proliferate in response to a human islet lysate was tested. The results from two clones are shown (FIG. 3A). Both proliferated in response to islet lysate, but not to spleen lysate from the same donor. Further experiments (FIG. 3B) showed that this response was blocked by antibodies specific for HLA DR, but not for HLA DQ.

EXAMPLE 9

The A-Chain Epitope is Presented by HLA DRB1 *0401, 0404, 0405

Figure 4:
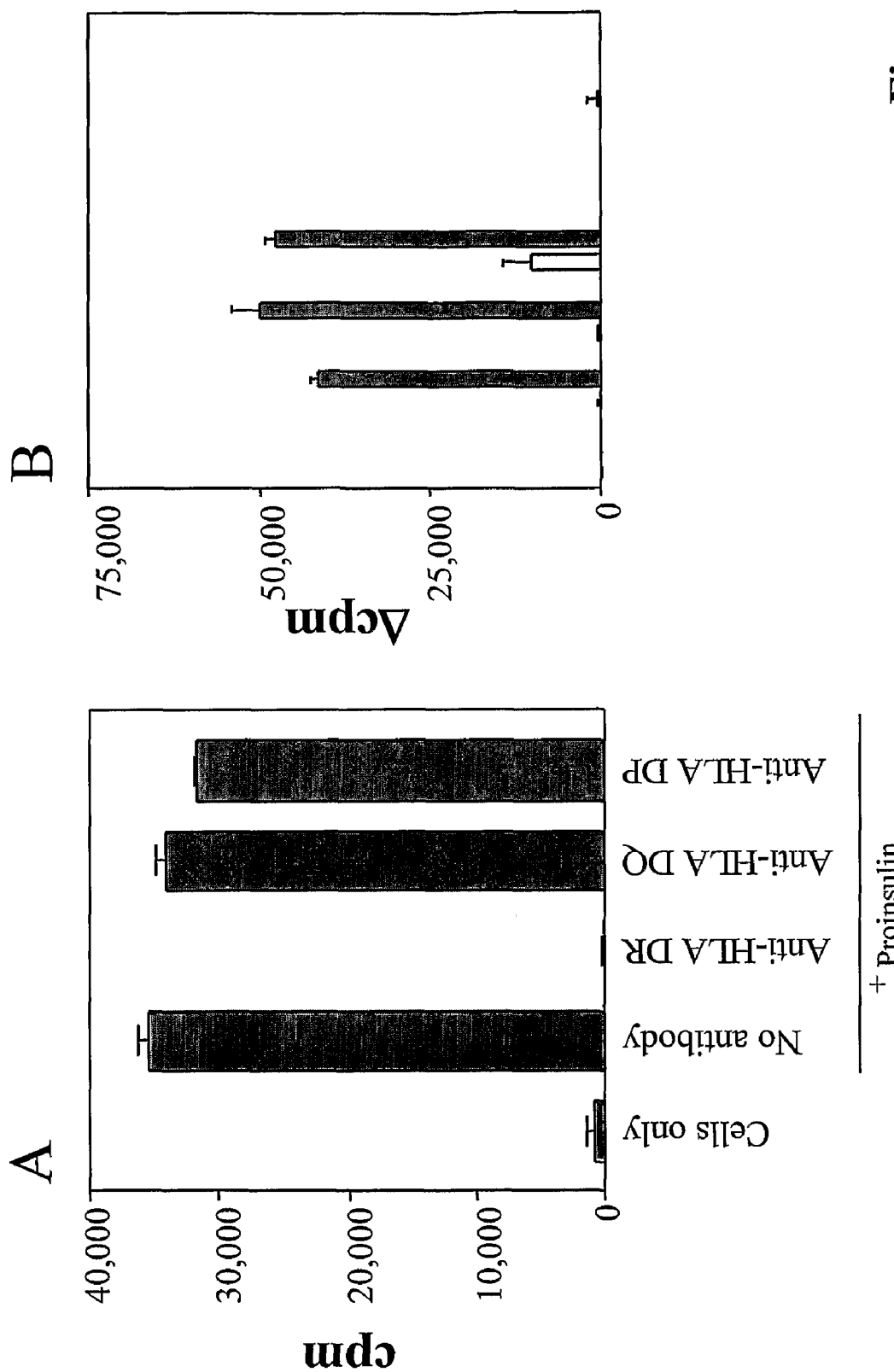
FIG. 4 is a graphical representation showing that the response of T-cell clones is HLA-DR4-restricted. (A) Insulin-specific T-cell clones were incubated with irradiated autologous PBMC ($1 \times 10^5$/well) without antigen (no antigen) or with 10 μg/ml proinsulin. Antibodies specific for HLA DR (L243), HLA DQ (SPV-L3) or HLA DP (B7/21) were added to a final concentration of 5 μg/ml. Similar results were obtained with three other insulin-specific clones. (B) Insulin-specific T-cell clones were incubated with irradiated (50 Gy), HLA-transfected BLS lines, that were pulsed with 100 μM A-chain peptide (KRGIVEQCCTSICSL; SEQ ID NO: 23) or an equal volume of solvent. Peptide-pulsed BLS cells ($1 \times 10^4$/well) were cultured with $2.5 \times 10^4$ insulin-specific T-cell clone/well. Proliferation of the BLS cells without T-cells (1,000-5,000 cpm) was subtracted. Similar results were obtained with three other insulin-specific clones.

The HLA type of the donor is shown in Table 5. The HLA molecule(s) that present(s) the epitope to the clones was determined in two steps. First, blocking with HLA-isotype-specific antibodies showed that proliferation of all clones was prevented by anti HLA-DR specific mAb (L243), but not by HLA DQ (SPV-L3)- or HLA DP (B7/21)-specific antibodies (FIG. 4A). Second, HLA restriction was confirmed using the panel of B-cell lines transfected with HLA βchain genes (FIG. 4B). Cells transfected with DRB1*0401 (DR4), DRB1*0404 (DR4) or DRB1*0405 (DR4) were all able to present peptide, whereas cells transfected with DRB4*0101 (DR52), DQB1*0201 (DQ2), DQB1*0302 (DQ8) were unable to present the agonist peptide. Similar results were obtained with a panel of HLA-typed EBV-transformed B cell lines. Hence, the HLA restriction is HLA DRB1*0401, 0404-05.

EXAMPLE 10

All Clones that Require the A-Chain Epitope Use the Same VαJα and VβJβ Sequences The TCR usage of A-chain epitope-specific T-cell clones was determined (Table 8). One clone uses $V\alpha \overline{3\text{-}1}1$ while the other three use $V\alpha 3\text{-}\overline{2}_1$. The same Jα4*01 is expressed by all clones. All clones use Vβ7-8*01 and Jβ1-1*01 The CDR3 sequence was identical for all but clone 4.19, which had different Vα and Vβ CDR3 sequences.

TABLE 8

Analysis of TCR Vα and Vβ gene usage by insulin-specific T-cell clones

| Clone | Vα | CDR3 | SEQ ID NO | Jα |
|---|---|---|---|---|
| 4,11 | 13-2*01 | CA-DSRAFSGGYNKLI-FG | 56 | 4*01 |
| 4,19 | 13-1*02 | CA-APILFSGGYNKLI-FG | 57 | 4*01 |

TABLE 8-continued

Analysis of TCR Vα and Vβ gene usage
by insulin-specific T-cell clones

| Clone | Vα | CDR3 | SEQ ID NO | Jα |
|---|---|---|---|---|
| 5,25 | 13-2*01 | CA-DSRAFSGGYNKLI-FG | 58 | 4*01 |
| 6,14 | 13-2*01 | CA-DSRAFSGGYNKLI-FG | 59 | 4*01 |

| Clone | Vβ | CDR3 | SEQ ID NO | Jβ |
|---|---|---|---|---|
| 4,11 | 7-8*01 | CASS-LYPGDLPEAF-FG | 60 | 1-1*01 |
| 4,19 | 7-8*01 | CASS-LIGSATEAF-FG | 61 | 1-1*01 |
| 5,25 | 7-8*01 | CASS-LYPGDLPEAF-FG | 62 | 1-1*01 |
| 6,14 | 7-8*01 | CASS-LYPGDLPEAF-FG | 63 | 1-1*01 |

EXAMPLE 11

The A-Chain Epitope Requires Adjacent Cysteines

Figure 5:
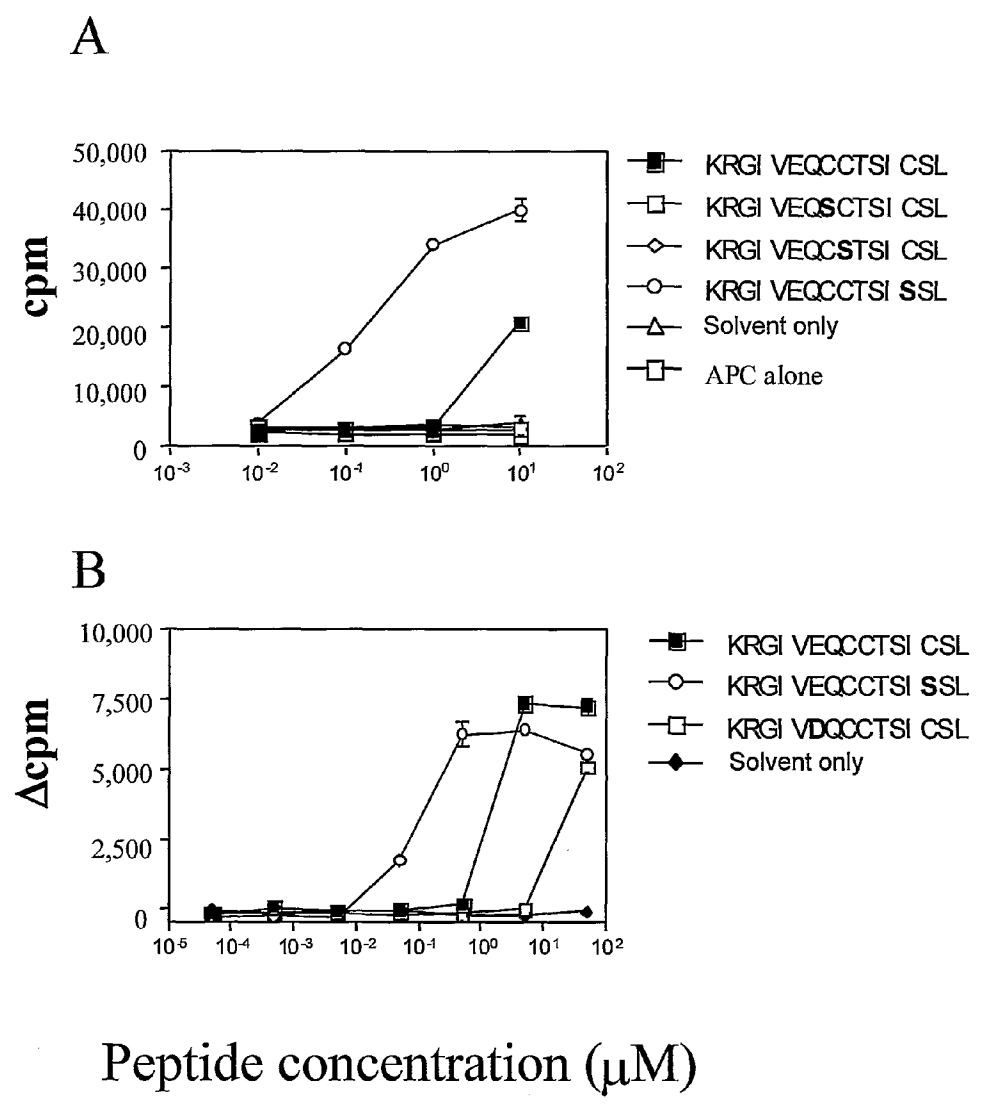

Peptides were tested in which cysteine was substituted by serine to determine the role of cysteine in creating the epitope recognized by the A-chain-specific clones. Substitution of either of the adjacent cysteines (A-6 and A-7) with serine completely abolished the capacity of the peptide to stimulate any of the T-cell clones (FIG. 5A), at peptide concentrations of up to 50 µM. Surprisingly, substitution of the cysteine at position A11 with serine increased the activity of the peptide 100-fold. A synthetic peptide corresponding to the sequence in mouse insulin II, which has aspartic acid instead of glutamic acid at position A4, was 10-fold less potent than the human peptide (FIG. 5B).

EXAMPLE 12

Adjacent Cysteines in the A-Chain Epitope Form an Intra-Chain Disulphide Bond

Figure 6A:
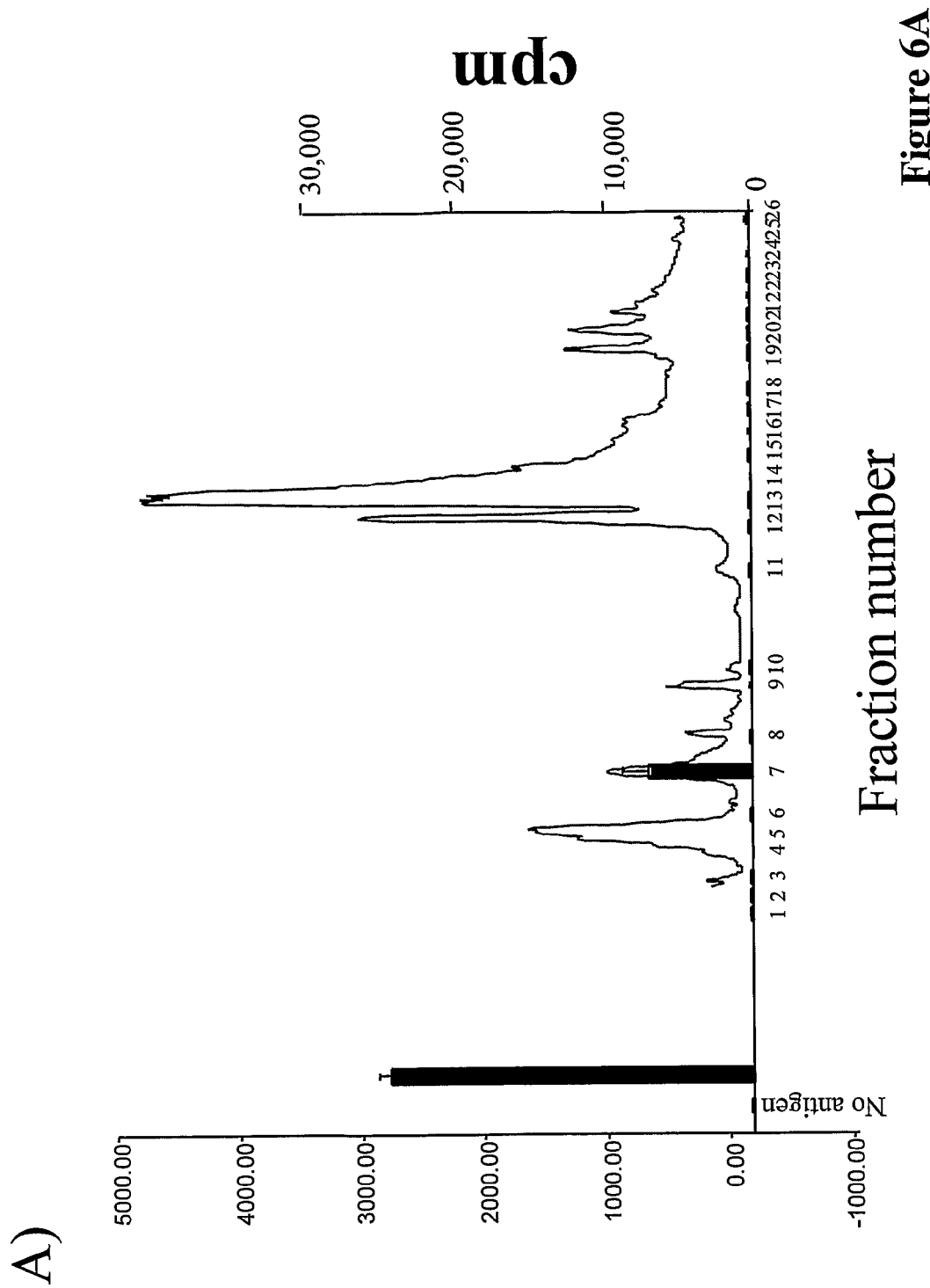
FIG. 6 is a graphical representation showing that the A-chain epitope contains an intra-chain disulphide bond. (A) To identify the modified epitope the S-13 peptide was incubated in serum-containing culture medium for 1 h at 37° C. This mixture was separated by RP-HPLC and 0.5 ml fractions collected. The profile shows absorbance at 214 nm. Solid bars show the proliferation of an insulin-specific T-cell clone in response to each fraction (1/400 dilution). A paraformaldehyde-fixed B-cell line that expresses HLA DRB1*0404 was used as the APC ($1 \times 10^4$/well). Proliferation was measured by $^3$H-thymidine incorporation during the final 18 hours of a 72 hr culture. (B) MALDI-QTOF mass spectrometry analysis of the parental peptide (KRGIVEQCCTSISSL; SEQ ID NO:26) and the active fraction (#7) from the medium modification experiment in (A). The active fraction contains a single peptide species two Daltons smaller than the S-13 peptide, consistent with an intra-chain disulphide bond between the cysteines at A6 and A7.
Figure 6B:
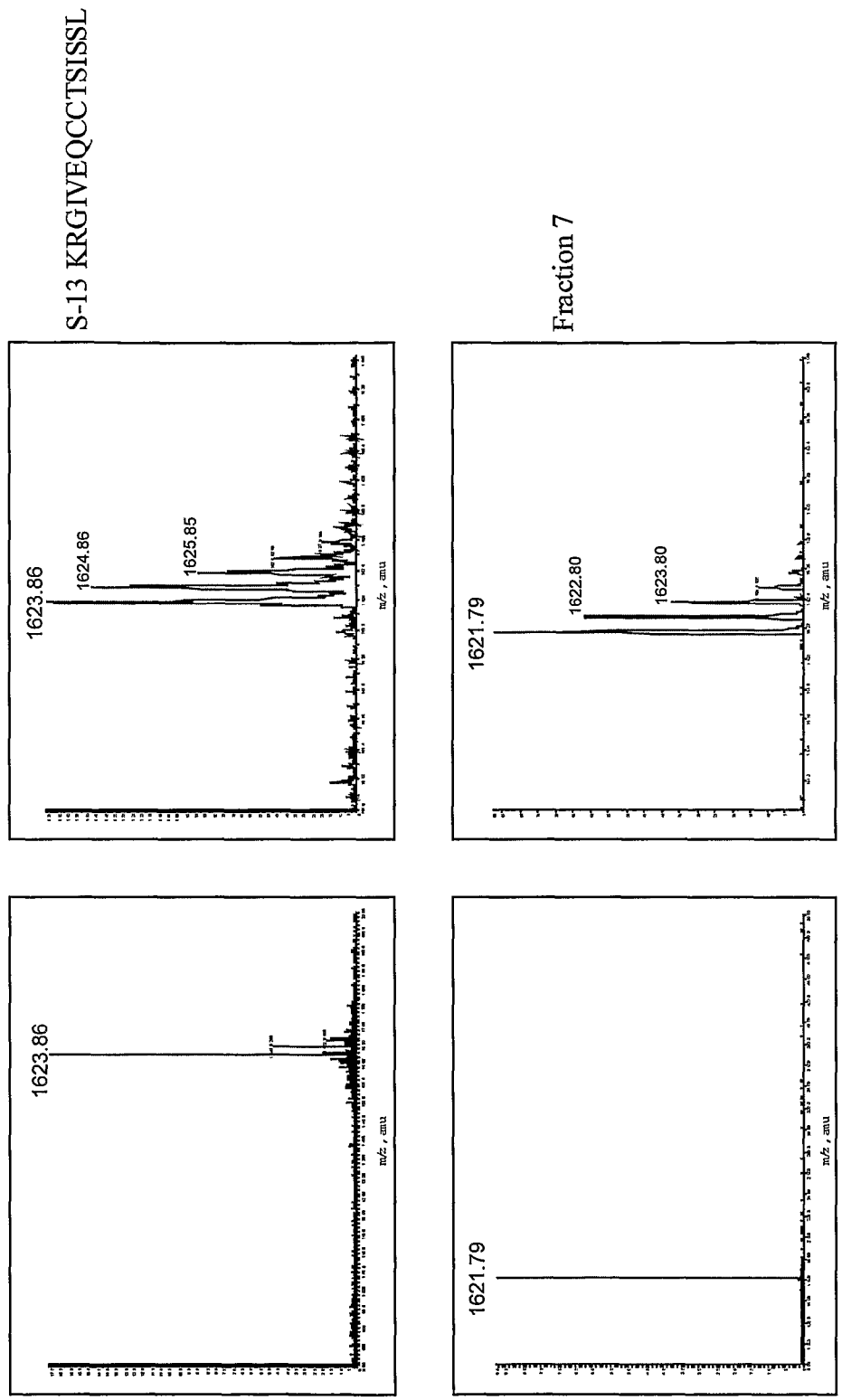

It is proposed that the epitope recognized by the T-cell clones requires PTM of the cysteines at positions A6 and A7. To investigate this, the capacity of paraformaldehyde-fixed and -unfixed APC to present the epitope (as a synthetic peptide) to the T-cell clones was compared. Fixation did not affect the response to the peptide. Therefore, it was concluded that the modification occurred spontaneously in the culture medium. To define the modification more exactly, peptide with a serine for cysteine substitution at residue 13 (A-11), referred to as S-13 was incubated, in culture medium and then used RP-HPLC to separate the components. The resultant fractions were tested for their capacity to stimulate proliferation of the clones. A single fraction (#7, FIG. 6A) was able to stimulate proliferation of the T-cell clones. No fractions stimulated proliferation when peptide with a serine for cysteine substitution at position A-6 was used. Analysis of the active fraction by mass spectroscopy (FIG. 6B) showed that it contained a single species that was 2 Daltons smaller than the parental S-13 peptide. Which is consistent with a loss of 2 hydrogen atoms. MS/MS analysis showed that this loss of 2 Daltons arose at the adjacent cysteine residues (Table 9). From this, it is concluded that the cognate epitope recognized by the T-cell clones contained an intra-chain disulphide bond between the two adjacent cysteines at positions A-6 and A-7.

TABLE 9

Assignment of b- seriesionsfor modified S-13 peptide
(SEQ ID NO: 26)

b1 b2 b3 b4 b5 b6 b7 b8 b9 b10 b11 b12 b13 b14 b15
K R G I V E Q C C T S I S S L

| b-series ions | Expected mass | Observed mass | Difference |
|---|---|---|---|
| b1 | 129.10 | 129.10 | 0.00 |
| b2 | 285.20 | 285.21 | 0.01 |
| b3 | 342.22 | 342.24 | 0.02 |
| b4 | 455.31 | 455.32 | 0.01 |
| b5 | 554.38 | 554.40 | 0.02 |
| b6 | 683.42 | 683.44 | 0.02 |
| b7 | 811.48 | 811.50 | 0.02 |
| b8 | 914.49 | 912.49 | −2.00 |
| b9 | 1017.50 | 1015.50 | −1.99 |
| b10 | 1118.54 | 1116.56 | −1.98 |
| b11 | 1205.58 | 1203.59 | −1.99 |
| b12 | 1318.66 | 1316.71 | −1.95 |
| b13 | 1405.69 | 1403.73 | −1.96 |
| b14 | 1492.72 | 1490.76 | −1.97 |
| b15 | 1605.81 | 1603.84 | −1.97 |

EXAMPLE 13

Recognition of the A-Chain Epitope is Blocked by Reduction of Disulphide Bonds

Figure 7:
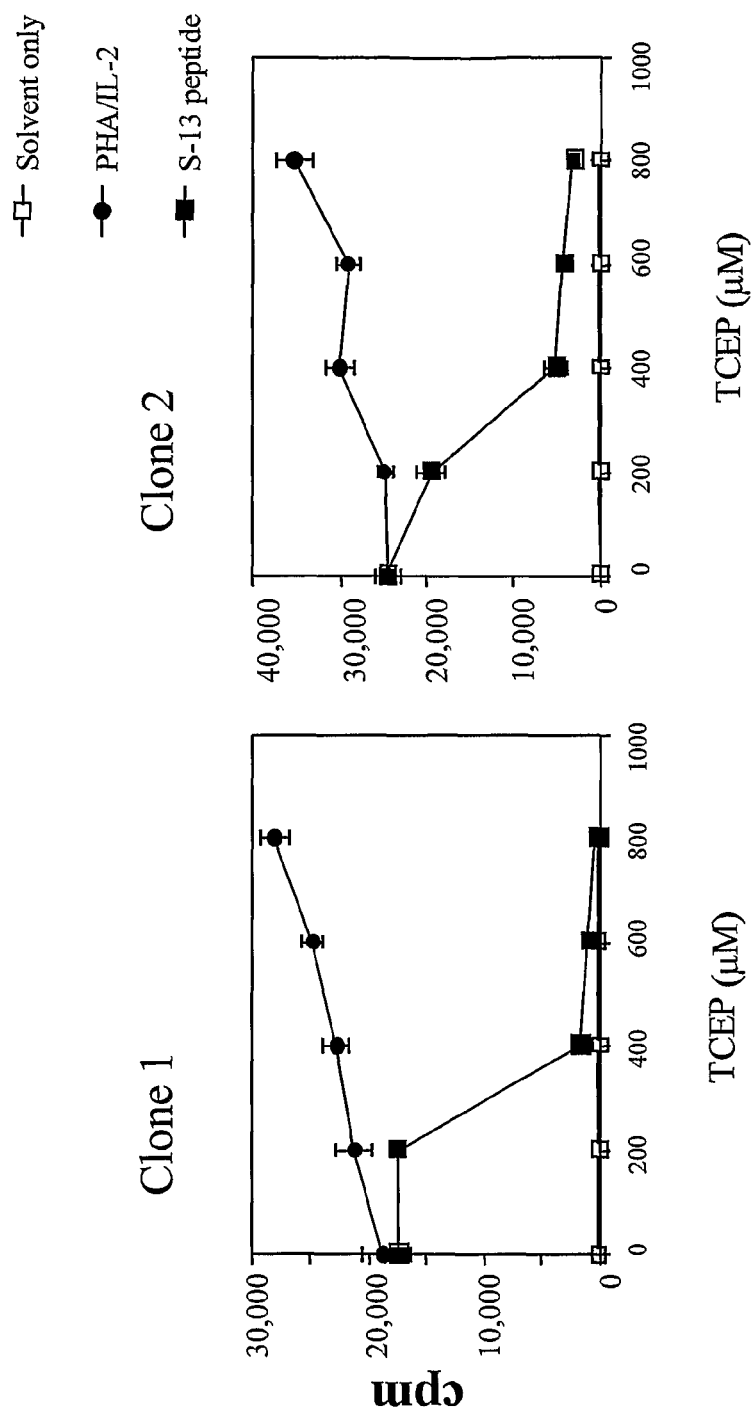
FIG. 7 is a graphical representation showing that reduction destroys the epitope. S-13 peptide (final 1 μM) was treated with freshly-prepared TCEP and diluted to the final concentrations shown. Each well included irradiated autologous PBMC ($5 \times 10^4$) and T-cell clone ($2.5 \times 10^4$/well). PHA (1.25 μg/ml), IL-2 (2.5 U/ml) and solvent alone were similarly prepared.

To confirm that an intra-chain disulphide bond is required for stimulation of the T-cell clones, the affect of the disulphide reducing agent Tris (2-carboxyethyl) phosphine hydrochloride (TCEP) on the response of T-cell clones to peptide S-13 was tested. With increasing concentrations of TCEP a dose-dependent inhibition of the response of the T-cell clones to peptide S-13 was observed (FIG. 7). The reduction in proliferation was not due to toxicity as the responses to PHA or IL-2 were not reduced, but rather slightly increased, by TCEP.

EXAMPLE 14

Figure 8:
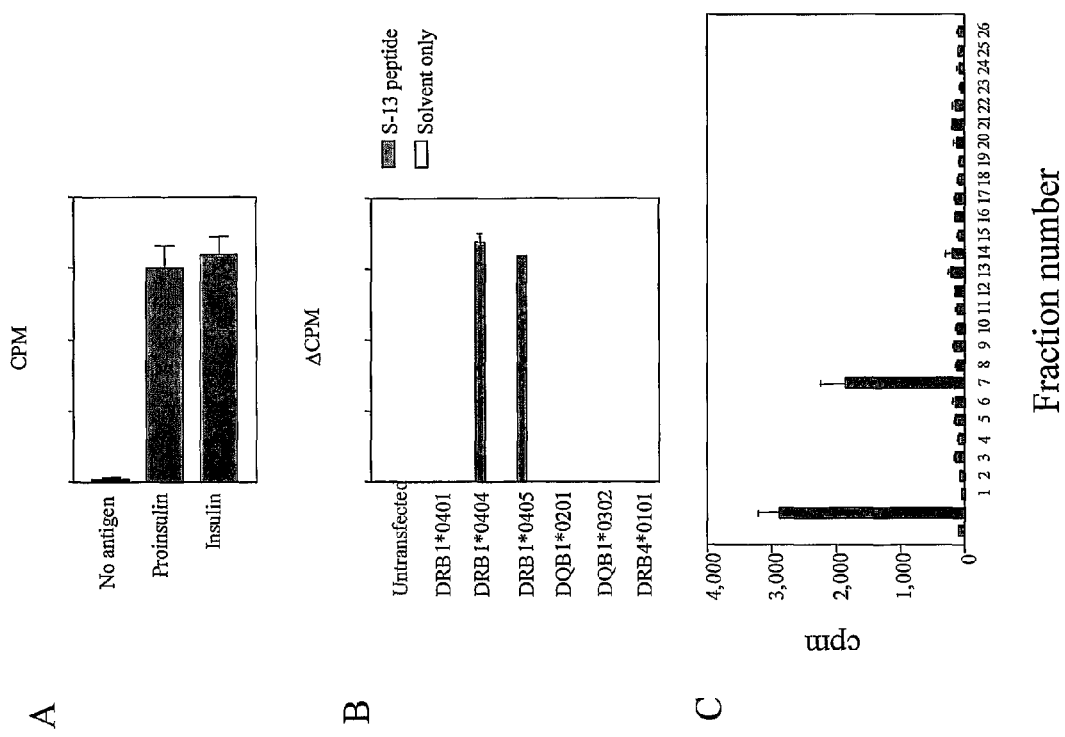
FIG. 8 is a graphical representation showing that T-cell clones from a pre-clinical type 1 diabetes donor recognize the same epitope. Three of 11 proinsulin-specific clones proliferated in response to insulin. (A) Proinsulin-specific T-cell clones were cultured with proinsulin (10 μg/ml) or insulin (10 μg/ml) or without antigen. One of three insulin-specific clones is shown. (B) Irradiated (50 Gy) B-cell lines transfected with the HLA genes shown were pulsed with S-13 peptide (100 μM) or solvent alone, for 2 h at 37° C. and washed. Each well contained $2.5 \times 10^4$ T-cells and $2.5 \times 10^4$ BLS lines. (C) A paraformaldehyde-fixed B cell line transfected with HLA DRB1*0404 was cultured with samples of RP-HPLC fractions used to identify the modification of the epitope recognized by the first series of clones. Each well contained $1 \times 10^4$ HLA DRB1*0404 transfected B cells, 1/100 dilution of each fraction and $2.5 \times 10^4$ cloned insulin-specific T-cells derived from the pre-clinical diabetic donor.

T-Cell Clones to the A-Chain Epitope Isolated from A Healthy Donor with Pre-Clinical T1D Eleven proinsulin-specific CD4$^+$ T-cell clones were isolated from an islet autoantibody-positive HLA DR4$^+$ donor at risk of developing T1D. Three of the clones proliferated in response to both proinsulin and insulin (see for example FIG. 8A). These clones. recognized the S-13 peptide in association with HLA DRB 1*0404-0405 (FIG. 8B). The response was targeted to the A-chain epitope with an intra-chain disulphide bond because this fraction from the RP-HLC column was the only one that stimulated this clone (FIG. 8C). Hence, T-cell clones specific for the post-translationally modified A-chain epitope were isolated from a donor at high risk for T1D never exposed to exogenous insulin.

EXAMPLE 15

Method for I-Ag7 Binding Experiment

Purification of I-Ag7. I-Ag7 protein was affinity-purified from detergent lysates of 4G4.7 B cell hybridoma cells by desorption from OX-6 mouse monoclonal antibody. The 4G4.7 B cell hybridoma was derived by polyethylene glycol (PEG)-induced fusion of NOD mouse T-cell-depleted splenocytes with the HAT-sensitive A20.2J lymphoma line. OX-6 is a mouse monoclonal IgG1 antibody against an invariant determinant of rat Ia, which also recognizes I-Ag7 but not I-Ad. Approximately 15 mg of OX-6 antibody was first bound to 4 ml of protein A-Sepharose 4 Fastflow (Pharmacia, Uppsala, Sweden) and then chemically cross-linked to the protein A with dimethyl pimelimidate dihydrochloride (Sigma Chemical Co., St. Louis, Mo.) in sodium borate buffer, pH 9.0. After 60 min at room temperature (RT), the reaction was quenched by incubating the Sepharose in 0.2 M ethanolamine, pH 8.0, for 60 min at RT. The suspension was washed thoroughly in PBS and stored in PBS, 0.02% sodium azide ($NaN_3$).

4G4.7 cells were harvested by centrifugation, washed in PBS, resuspended at $10^8$ cells/ml of lysis buffer, and then allowed to stand at 4° C. for 120 min. The lysis buffer was 0.05 M sodium phosphate, pH 7.5, containing 0.15 M NaCl, 1% (vol/vol) NP40 detergent and the following protease inhibitors: 1 mM phenylmethylsulphonyl fluoride, 5 mM -amino-n-caproic acid and 10 μg/ml each of soybean trypsin inhibitor, antipain, pepstatin, leupeptin and chymotrypsin. Lysates were cleared of nuclei and debris by centrifugation at 27,000 g for 30 min and stored as such if not immediately processed further. To the postnuclear supernatant was added 0.2 vol of 5% sodium deoxycholate (DOC). After mixing at 4° C. for 10 min, the supernatant was centrifuged at 100,000 g at 4° C. for 120 min, carefully decanted, and filtered through a 0.45-gm nylon membrane. The lysate of 5×1010 4G4.7 cells was gently mixed overnight at 4° C. with 4 ml of OX6-protein A-Sepharose, and the suspension then poured into a column and washed with at least 50 vol each of buffers A, B, and C. Buffer A was 0.05 M Tris, pH 8.0, 0.15 M NaCl, 0.5% NP40, 0.5% DOC, 10% glycerol, and 0.03% $NaN_3$; buffer B was 0.05 M Tris, pH 9.0, 0.5 M NaCl, 0.5% NP-40, 0.5% DOC, 10% glycerol, and 0.03% $NaN_3$; buffer C was 2 mM Tris, pH 8.0, 1% octyl-D-glucopyranoside (OGP), 10% glycerol, and 0.03% NaN3. Bound I-Ag7 was eluted with 50 mM diethylamine HCl, pH 11.5 in 0.15 M NaCl, 1 mM EDTA, 1% OGP, 10% glycerol, and 0.03% NaN3, and immediately neutralized with 1 M Tris.

Peptide Synthesis. Peptides were synthesized with a multiple peptide synthesizer (model 396; Advanced ChemTech, Louisville, Ky.) using Fmoc chemistry and solid phase synthesis on Rink Amide resin. All acylation reactions were effected with a threefold excess of activated Fmoc amino acids, and a standard coupling time of 20 min was used. Each Fmoc amino acid was coupled at least twice. Cleavage and side chain deprotection was achieved by treating the resin with 90% trifluoroacetic acid, 5% thioanisole, 2.5% phenol, 2.5% water. The indicator peptide for the binding assay was biotinylated before being cleaved from. resin by coupling two 6-aminocaproic acid spacers on the NH2 terminus and one biotin molecule sequentially, using the above-described procedure. Individual peptides were analyzed by reverse-phase HPLC and those used in this study were routinely 85% pure.

I-Ag7 Peptide-binding Assay. Peptides were dissolved at 10 mM in DMSO and diluted into 20% DMSO/PBS for assay. Indicator I-Ag7 binding peptide, HEL 10-23, was synthesized with a biotin molecule and two spacer residues at the NH2 terminus. Approximately 200 nM of this biotinylated HEL peptide and each test peptide in seven concentrations ranging from 50 μM to 50 pM, were coincubated with ~200 ng of I-Ag7 protein in U-bottomed polypropylene 96-well plates (Costar Serocluster, Costar Corp., Cambridge, Mass.) in binding buffer at RT. The binding buffer was 6.7 mM citric phosphate, pH 7.0, with 0.15 M NaCl, 2% NP-40, 2 mM EDTA, and the protease inhibitors as used in the lysis buffer. After a minimum of 24 h, each incubate was transferred to the corresponding well of an ELISA plate (Nunc Maxisorp, Nunc, Roskilde, Denmark) containing prebound OX-6 antibody (5 pg/ml overnight at 4° C., followed by washing). After incubation at RT for at least 2 h, and washing, bound biotinylated peptide-I-Ag7 complexes were detected colorimetrically at 405 nm after reaction with streptavidin-alkaline phosphatase and paranitrophenolphosphate. Competition binding curves were plotted and the affinity of peptide for I-Ag7 was expressed as an inhibitory concentration 50 (IC50), the concentration of peptide required to inhibit the binding of bio-HEL 10-23 by 50%.

Results

I-Ag7 Purification and Binding Assay

Approximately 2 mg of protein, estimated by Coomassie blue binding (Bio Rad Protein assay), was purified from 5×1010 4G4.7 cells. In SDS-PAGE, the majority (>95%) of the protein was resolved as two bands of molecular weight ~33,000 and ~28,000 that correspond to the and subunits, respectively, of mouse class II MHC molecules. The competition binding assay with purified I-Ag7 was sensitive and specific, and highly reproducible; in 15 separate assays the mean±SD of the IC50 for competition between biotinylated and unlabeled HEL 10-23 was 295±72 nM.

Peptides overlapping by four residues and spanning the entire sequence of human proinsulin were tested for binding to I-Ag7, and were inspected for presence of binding motif (see Table 10). The proinsulin peptide aa. 65-79, from the A-chain of insulin, in which the cysteines were replaced for the binding studies by alanines, bound with moderately high affinity (400 nM) to I-Ag7.

Peptides overlapping by four residues and spanning the entire sequence of human proinsulin were tested for binding to I-Ag7, and inspected them for presence of the binding motif. The proinsulin peptide aa 65-79, from the A-chain of insulin, in which the cysteines were replaced for the binding studies by alanines, bound with moderately high affinity (400 nM) to I-Ag7.

Mice:
NOD/Jax (F), 10-12 mice per group
Peptides:
Mouse proinsulin II amino acids C53-A7 (LQTLALEVAQQKRGIVDQCC (SEQ ID NO:31)).
Mouse proinsulin II amino acids C64-A13 (KRGIVDQCCTSICSL (SEQ ID NO:32)).
Mouse proinsulin II amino acids C64-A13 with cysteine at A6, A7 and All substituted for serine (KRGIVDQSSTSISSL (SEQ ID NO:33)).

Mice were treated with 10 μg of peptide, in 5 μl of phosphate buffered saline (PBS). Three series of treatments were administered, each for 10 consecutive days, starting when the mice were 21, 50 and 100 days old.

Once the mice reached 100 days of age their urine glucose was measured. Mice that had elevated urine-glucose concentrations (>11 mM) were re-tested, those with two consecutive urine glucose concentrations above 11 mM were considered diabetic.

Table 10

Overlapping Human Proinsulin Peptides Tested for Binding to I-A^g7

| Peptide sequence | | IC$_{50}$ (nM) | Motif | Seq ID NO |
|---|---|---|---|---|
| (1-15) | F V N Q H L A G S H L V E A L | 7,000 | - | 36 |
| (5-19) | H L A G S H L V E A L Y L V A | 30,000 | + | 37 |
| (9-23) | S H L V E A L Y L V A G E R G | 1,000 | + | 38 |
| (13-27) | E A L Y L V A G E R G F F Y T | 4,000 | - | 39 |
| (17-31) | L V A G E R G F F Y T P K T R | >50,000 | + | 40 |
| (21-35) | E R G F F Y T P K T R R E A E | 1,000 | + | 41 |
| (25-39) | F Y T P K T R R E A E D Q L V | 1,000 | + | 42 |
| (29-43) | K T R R E A E D L Q V G Q V E | 7,000 | - | 43 |
| (33-47) | E A E D L Q V G Q V E L G G G | >50,000 | - | 44 |
| (37-51) | L Q V G Q V E L G G G P G A G | >50,000 | - | 45 |
| (41-55) | Q V E L G G G P G A G S L Q P | 6,000 | - | 46 |
| (45-59) | G G G P G A G S L Q P L A L E | 200 | + | 47 |
| (49-63) | G A G S L Q P L A L E G S L Q | 1,000 | + | 48 |
| (53-67) | L Q P L A L e G S L Q K R G I | 25,000 | - | 49 |
| (57-71) | A L e G S L Q K R G U V E Q A | 15,000 | - | 50 |
| (61-75) | S L Q K R G I V E Q A A T S I | 12,000 | - | 51 |
| (65-79) | R G U V E G A A T S I A S L Y | 400 | + | 52 |
| (69-83) | E Q A A T S I A S L T Q L E N | 12,000 | + | 53 |
| (73-86) | T S I A S L Y Q L E N Y A N | 10,000 | + | 54 |

Residues well tolerated at the p6 or p9 anchor positions are bolded; weakly tolerated are underlined; non-tolerated are bolded in lower case. Cysteines have been substituted by alanine (A in italics).

EXAMPLE 16

Prevention of Diabetes in NOD Mice

The aim of this Example is to investigate human T-cell response to A1-13 epitope and the use of the NOD mouse model to determine the efficacy of peptide encompassing this epitope for prevention of type 1 diabetes (T1D).
Introduction/Rationale T-cell responses to the islet autoantigens proinsulin and GAD can be detected in healthy subjects (Mannering et al, *Ann N.Y. Acad Sci* 1037:16-21, 2004). While the epitope specificity of these responses has not been determined it is possible that certain epitopes are associated with diabetes while other epitopes are recognized by T-cells from healthy subjects.

The non obese diabetic (NOD) mouse spontaneously develops autoimmune diabetes and is a widely used model of human type 1 diabetes. Intranasal delivery of insulin protein (Harrison et al, *J Exp Med* 185:1013-1021, 1996) or a proinsulin peptide spanning the B-C chain junction (Martinez et al, *J Clin Invest* 111:1365-1371, 2003) has been shown to prevent diabetes in the NOD mouse. The intranasal proinsulin B-C chain peptide induces regulatory, anti-diabetogenic CD4⁺ T-cells. To elicit a CD4⁺ T-cell response a peptide must first bind to an MHC class II molecule. This mouse expresses a single MHC class II molecule, I-Ag7.

The peptide KRGIVEQCCTSICSL (SEQ ID NO: 2332), or the murine homologue, KRGIVDQCCTSICLS (SEQ ID NO:32), are referred to as the A1-13 epitope, because these peptides encompass the minimum epitope described herein (GIVEQCCTSICSL (SEQ ID NO:34), or in the mouse GIVDQCCTSICSL (SEQ ID NO:35)).

Methods:

Analysis of clones from healthy HLA DR4⁺ subjects: CD4⁺ T-cell clones that proliferate in response to proinsulin were isolated as described (Mannering et al, *J Immunol Methods* 298:83-92, 2005). Each clone was cultured with irradiated antigen presenting cells (APC) and either no antigen, proinsulin (10 µg/ml) or A1-13 peptide (KRGIVEQC-CTSICSL SEQ NO: 23) (10 µM). Responses to a peptide encompassing the A1-13 epitope were detected by incorporation of ³H-thymidine during the final 16 hours of culture.

I-Ag7 binding: I-Ag7 binding was determined by competition for a biotinylated reporter peptide (bio-HEL10-23), known to bind I-Ag7. Proinsulin peptides were incubated in serial dilution with a fixed concentration of bio-HEL 10-23 (For full details see Attachment 1). High-affinity peptides inhibit binding of the reporter peptide at low concentrations (~100-500 nM), whereas low or non-binding peptides inhibited at high concentrations (>2.0 µM). Cysteine residues in the proinsulin peptides used for the I-Ag7 binding were substituted for alanine to avoid oxidative modifications.

Peptide therapy: NOD mice were used to test the capacity of peptide encompassing the A1-13 epitope to prevent diabetes (see protocol in Attachment 2). Mice were treated by intranasal delivery of a peptide of the following peptides (KRGIVDQCCTSICSL (SEQ ID NO:32)), or a similar peptide where the cysteines were substituted by serine (KRGIVDQSSTSISSL (SEQ ID NO:33)), or a control peptide (LQTLALEVAQQKRGIVDQCC (SEQ ID NO: 31) The cysteine residues at positions A6 and A7 are required for formation of a vicinal disulfide bond and recognition by human CD4+ T-cell clones (as shown previously). Binding of the peptide encompassing the Al-13 epitope to HLA DR4 is not affected by substituting cysteine for serine. The murine form homologue of the A1-13 peptide binds to I-Ag7, as shown below, when cysteine has been replaced with alanine. Diabetes incidence was monitored for >240 days by testing for urine glucose each week from 100 days of age. Diabetes was confirmed by two consecutive daily blood glucose concentrations >11 mM.

Results

Figure 9:
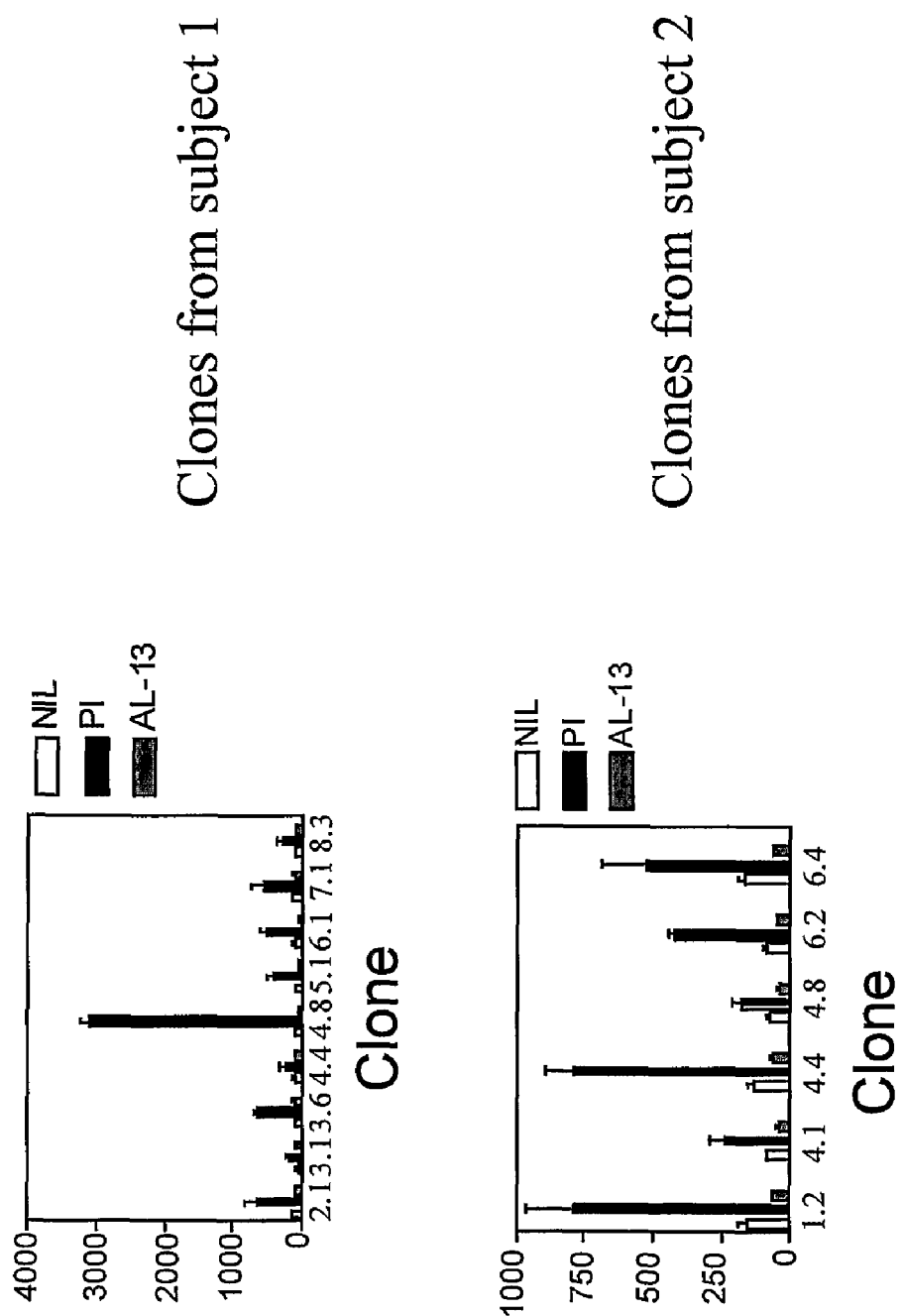
FIG. 9 is a graphical representation showing that clones from healthy subjects do not recognize the A1-13 epitope.

Analysis of clones from healthy HLA DR4+ subjects: Fifteen clones that recognize proinsulin from two HLA DR4+ healthy subjects were tested for their capacity to proliferate in response to proinsulin and a peptide encompassing the A1-13 epitope (KRGIVEQCCTSICSL (SEQ ID NO:23)). None of the clones that proliferated in response to proinsulin proliferated in response to a peptide encompassing the A1-13 epitope, see FIG. 9.

Peptide Binding to I-Ag7

A peptide encompassing the human A-chain epitope with the cysteines replaced by alanine (RGIVEQAATSIASL (SEQ ID NO: 55)) bound with high-to-moderate affinity, $IC_{50}$ of 400 nM (See Table 10), to I-Ag7.

Prevention of T1D in the NOD Mice

Figure 10:
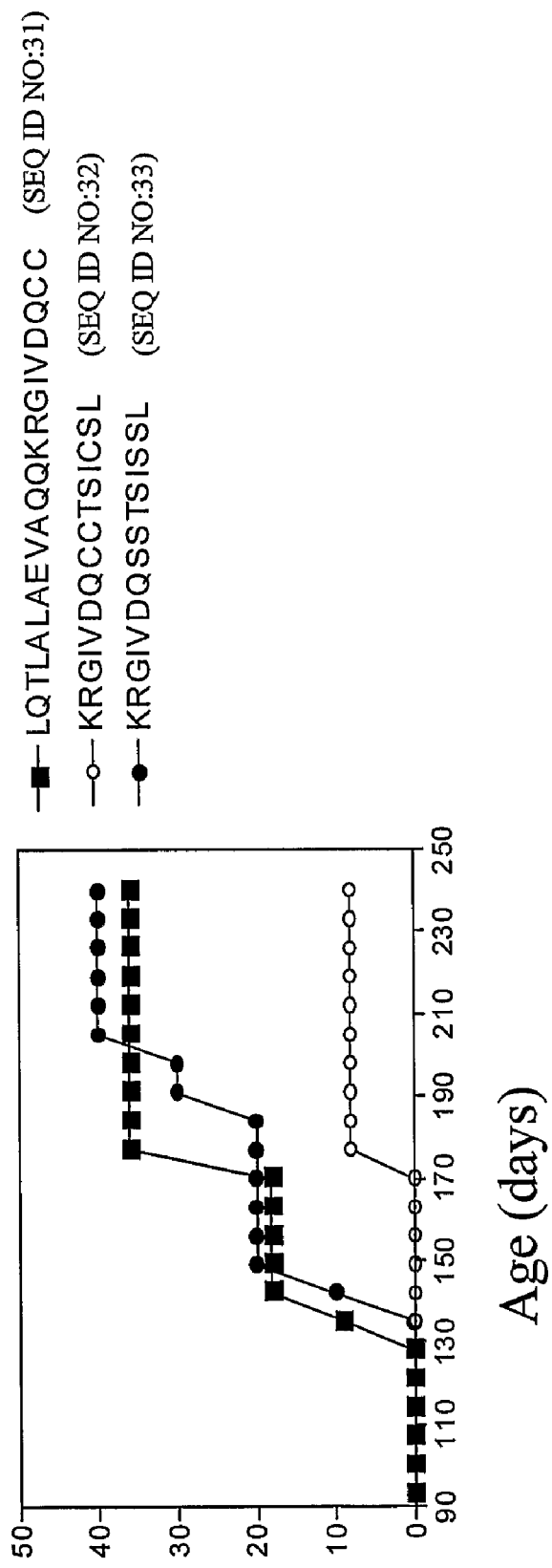
FIG. 10 is a graphical representation showing that A1-13 peptide prevents diabetes in NOD mice.

NOD mice were treated with peptide encompassing the A1-13 epitope, variants of the epitope, or an irrelevant peptide from proinsulin. The incidence of diabetes was monitored until the mice were 240 days old. Of the mice treated with the a peptide encompassing the A1-13 epitope (KRGIVDQCCTSICSL (SEQ ID NO:32)), one of 12 developed diabetes (8.3%), whereas four of 10 treated with a similar peptide with the cysteines replaced with serine (KRGIVDQSSTSISSL (SEQ ID NO:33)) developed diabetes (40%). When mice were treated with another peptide from proinsulin (LQTLALEVAQQKRGIVDQCC (SEQ ID NO: 31)) four out of 11 (36.4%) developed diabetes (FIG. 10).

(a) Analysis of Proinsulin-Specific T-Cell Clones from Healthy Donors

This shows that clones isolated from healthy subjects, who express HLA DR4, do not respond to the A1-13 epitope. This suggests that responses to this epitope may only be found in people at risk of T1D or those who already have T1D.

(b) Binding to I-Ag7

These data show that the peptide encompassing the A1-13 epitope binds to the MHC class II molecule, I-Ag7. Intranasal treatment with a peptide encompassing the AI-13 epitope reduced diabetes development in NOD mice, but only if cysteines were present. This supports the role of adjacent cysteine residues at A6 and A7 forming a vicinal-disulfide bond in the formation of the epitope recognized by T-cells that mediate protection against diabetes.

(c) Peptide Therapy for Preventing T1D in NOD Mice

The NOD mouse is a useful model for analysing the mechanism of peptide-mediated protection against type 1 diabetes. These data show that treatment with this peptide can prevent the development of diabetes in susceptible animals. This supports the use of peptide(s) encompassing the A1-13 epitope for the prevention of T1D in susceptible people.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Alleva, et al., *J. Clin. Invest.* 107:173-180, 2001
Anderson et al., *Nat. Med.* 6:337-442, 2000
Bodanszky, *Principles of Peptide Synthesis*, Springer Verlag 1984
Congia et al., *Proc. Natl. Acad. Sci. USA* 95:3833-3838, 1998
Cowley and Mackin, *FEBS Lett* 402:124-130, 1997
Doyle and Mamula, *Trends. Immunol.* 22:443-449, 2001
Douillard and Hoffman, Basic Facts about Hybridomas, in *Compendium of Immunology* Vol. II, ed. by Schwartz, 1981
Durinovic-Bello et al., *J. Autoimmun* 18:55-66, 2002
Eisenbarth et al., *J. Autoimmun.*, 5Suppl. A:241-246, 1992
Erickson et al., *Science* 249: 527-533, 1990
Harrison et al, *J Exp Med* 185:1013-1021, 1996
Harrison, L. C., *Pediatr Diabetes,* 2:71-82, 2001
Haunkapiller et al, *Nature* 310:105-11, 1984
Haunkapiller et al, *Nature* 310:105-11, 1984
Hodgson (*BioTechnology* 9: 19-21, 1991
Houben-Weyl, *Methoden der organischen Chemie.* Vol. 15/1 and 15/2
Kitutani et al., *Adv. Immunol.*, 51:285-322, 1992
Kohler and Milstein, *Nature* 256: 495-499, 1975
Kohler and Milstein, *European Journal of Immunology* 6: 511-519, 1976
Kunkel et al., *Mol. Cell. Biochem.* 34:3, 1981
Lieberman et al., *Tissue Antigens* 62:359-377, 2003
Lucassen et al., *Nat. Genet,* 4:305-310, 1993
Mannering et al, *Ann N.Y. Acad Sci* 1037:16-21, 2004
Mannering et al, *J Immunol Methods* 298:83-92, 2005
Martinez et al, *J Clin Invest* 111:1365-1371, 2003
Molberg et al., *Nat. Med.* 4:713-717, 1998
Munder et al., *Appl. Microbiol. Biotechnol.* 52: 311-320, 1999
Narendran et al., *Autoimmun. Rev,* 2:204-210, 2003
Ott et al., *J. Chin. Immunol.* 24:327-339, 2004
Pierce Chemical Co. *Pierce Immuno Technology Catalog and Handbook,* 1990
Pugliese et al., *Type* 1 *diabetes. Molecular, cellular, and clinical immunology.*, Oxford University Press: New York, Oxford:134-152, 1996
Pugliese et al., *Nat Genet,* 15:293-297, 1997
Rudy, et al., *Mol Med,* 1:625-633, 1995
Raju et al., *Hum. Immunol* 58:21-29, 1997
Schloot et al., *J. Autoimmun* 11:169-175, 1998
Semana et al., *J. Autoimmun* 12:259-267, 1999
Shapiro, *"Practical flow cytometry"*, 3$^{rd}$ ed. Brisbane, Wiley-Liss, 1995
Shapiro et al., N *Engl. J. Med.* 343:230-238, 2000
Stewart and Young, *Solid Phase Peptide Synthesis,* 2$^{nd}$ Ed., Pierce Chemical Co., Rockford III, 1984
Tait et al., *Hum. Immunol,* 42:116-122, 1995
Verge, et al., *Diabetes* 47:1857-1866, 1998
Wells, *Methods Enzymol.* 202: 2699-2705, 1991
Yagi et al., *Eur. J. Immunol.* 22:2387-2393, 1992
Young et al., *Nat. Biotechnol.* 16: 946-950, 1998
Ziegler et al., *Diabetes* 40:709-714, 1991

What is claimed is:

1. An isolated peptide consisting of a complete amino acid sequence selected from the group consisting of SEQ ID NO: 23, SEQ ID NO: 26, SEQ ID NO: 27 and SEQ ID NO: 35.

2. The isolated peptide of claim 1 consisting of SEQ ID NO: 23.

3. The isolated peptide of claim 1 consisting of SEQ ID NO: 27.

4. A cytotoxic T-cell targeting agent comprising the peptide of claim 1 bound, fused or otherwise associated with a cytotoxic moiety.

5. A pharmaceutical composition comprising the peptide of claim 1 and one or more pharmaceutically acceptable carriers and/or diluents.

6. The isolated peptide of claim 1 consisting of SEQ ID NO: 26.

* * * * *

SEQUENCE LISTING

<160> NUMBER OF SEQ ID NOS: 65

<210> SEQ ID NO 1
<211> LENGTH: 110
<212> TYPE: PRT
<213> ORGANISM: Homo sapiens

<400> SEQUENCE: 1

Met Ala Leu Trp Met Met Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Ser His Leu Val Glu Ala Leu Tyr Leu Val Cys Gly Glu Arg Gly
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide

<400> SEQUENCE: 3

Phe Phe Tyr Thr Pro Lys Thr Arg Arg Glu Ala Glu Asp
1               5                   10

<210> SEQ ID NO 4
<211> LENGTH: 24
<212> TYPE: PRT
<213> ORGANISM: Artificial Sequence
<220> FEATURE:
<223> OTHER INFORMATION: Synthetic peptide

<400> SEQUENCE: 4

Ala Leu Tyr Leu Val Cys Gly Glu Arg Gly Phe Phe Tyr Thr Pro Lys
1               5                   10                  15

Thr Arg Arg Glu Ala Glu Asp Leu
            20

<210> SEQ ID NO 5
<211> LENGTH: 17
<212> TYPE: PRT
<213> ORGANISM: Artificial Sequence

```
<220> FEATURE:
<223> OTHER INFORMATION: Synthetic peptide

<400> SEQUENCE: 5

Leu Ala Leu Glu Gly Ser Leu Gln Lys Arg Gly Ile Val Glu Gln Cys
1               5                   10                  15

Cys

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Leu Val Glu Ala Leu Tyr Leu Val Cys Gly Glu Arg Gly Phe Phe Tyr
1               5                   10                  15

Thr

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Gly Glu Arg Gly Phe Phe Tyr Thr Pro Lys Thr Arg Arg Glu Ala
1               5                   10                  15

<210> SEQ ID NO 8
<211> LENGTH: 18
<212> TYPE: PRT
<213> ORGANISM: Artificial Sequence
<220> FEATURE:
<223> OTHER INFORMATION: Synthetic peptide

<400> SEQUENCE: 8

Thr Pro Lys Thr Arg Arg Glu Ala Glu Asp Leu Gln Val Gly Gln Val
1               5                   10                  15

Glu Leu

<210> SEQ ID NO 9
<211> LENGTH: 17
<212> TYPE: PRT
<213> ORGANISM: Artificial Sequence
<220> FEATURE:
<223> OTHER INFORMATION: Synthetic peptide

<400> SEQUENCE: 9

Gln Val Gly Gln Val Glu Leu Gly Gly Gly Pro Gly Ala Gly Ser Leu
1               5                   10                  15

Gln

<210> SEQ ID NO 10
<211> LENGTH: 19
<212> TYPE: PRT
<213> ORGANISM: Artificial Sequence
<220> FEATURE:
<223> OTHER INFORMATION: Synthetic peptide

<400> SEQUENCE: 10

Leu Glu Gly Ser Leu Gln Lys Arg Gly Ile Val Glu Gln Cys Cys Thr
1               5                   10                  15
```

Ser Ile Cys

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

```
Cys Thr Ser Ile Cys Ser Leu Tyr Gln Leu Glu Asn Tyr Cys Asn
1               5                   10                  15
```

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

```
Leu Val Glu Ala Leu Tyr Leu Val Cys Gly Glu Arg Gly Phe Phe Tyr
1               5                   10                  15

Thr
```

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

```
Glu Asp Leu Gln Val Gly Gln Val Glu Leu Gly Gly Gly Pro Gly Ala
1               5                   10                  15
```

<210> SEQ ID NO 14
<211> LENGTH: 24
<212> TYPE: PRT
<213> ORGANISM: Artificial Sequence
<220> FEATURE:
<223> OTHER INFORMATION: Synthetic peptide

<400> SEQUENCE: 14

```
Met Ala Leu Trp Met Arg Leu Leu Pro Leu Leu Ala Leu Leu Ala Leu
1               5                   10                  15

Trp Gly Pro Asp Pro Ala Ala Ala
            20
```

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide

<400> SEQUENCE: 15

```
Gly Glu Arg Gly Phe Phe Tyr Thr Pro Lys Thr Arg Arg Glu Ala Glu
1               5                   10                  15

Asp Leu Gln Val
            20
```

<210> SEQ ID NO 16
<211> LENGTH: 19
<212> TYPE: PRT

```
<213> ORGANISM: Artificial Sequence
<220> FEATURE:
<223> OTHER INFORMATION: Synthetic peptide

<400> SEQUENCE: 16

Leu Ala Leu Trp Gly Pro Asp Pro Ala Ala Ala Phe Val Asn Gln His
1               5                   10                  15

Leu Cys Gly

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

Gly Glu Arg Gly Phe Phe Tyr Thr Pro Lys Thr Arg Glu Ala Glu
1               5                   10                  15

Asp Leu Gln Val
            20

<210> SEQ ID NO 18
<211> LENGTH: 19
<212> TYPE: PRT
<213> ORGANISM: Artificial Sequence
<220> FEATURE:
<223> OTHER INFORMATION: Synthetic peptide

<400> SEQUENCE: 18

Gly Ser Leu Gln Pro Leu Ala Leu Glu Gly Ser Leu Gln Lys Arg Gly
1               5                   10                  15

Ile Val Glu

<210> SEQ ID NO 19
<211> LENGTH: 16
<212> TYPE: PRT
<213> ORGANISM: Artificial Sequence
<220> FEATURE:
<223> OTHER INFORMATION: Synthetic peptide

<400> SEQUENCE: 19

Leu Ala Leu Leu Ala Leu Trp Gly Pro Asp Pro Ala Ala Ala Phe Val
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic peptide

<400> SEQUENCE: 20

Pro Ala Ala Ala Phe Val Asn Gln His Leu Cys Gly Ser His Leu Val
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: Synthetic peptide

<400> SEQUENCE: 21

Gly Ala Gly Ser Leu Gln Pro Leu Ala Leu Glu Gly Ser Leu Gln Lys
1               5                   10                  15
```

Arg Gly

```
<210> SEQ ID NO 22
<211> LENGTH: 17
<212> TYPE: PRT
<213> ORGANISM: Artificial Sequence
<220> FEATURE:
<223> OTHER INFORMATION: Synthetic peptide

<400> SEQUENCE: 22

Ser Leu Gln Lys Arg Gly Ile Val Glu Gln Cys Cys Thr Ser Ile Cys
1               5                   10                  15

Ser

<210> SEQ ID NO 23
<211> LENGTH: 15
<212> TYPE: PRT
<213> ORGANISM: Artificial Sequence
<220> FEATURE:
<223> OTHER INFORMATION: Synthetic human A-chain peptide

<400> SEQUENCE: 23

Lys Arg Gly Ile Val Glu Gln Cys Cys Thr Ser Ile Cys Ser Leu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic human S-8 peptide

<400> SEQUENCE: 24

Lys Arg Gly Ile Val Glu Gln Ser Cys Thr Ser Ile Cys Ser Leu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic human S-9 peptide

<400> SEQUENCE: 25

Lys Arg Gly Ile Val Glu Gln Cys Ser Thr Ser Ile Cys Ser Leu
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: synthetic human S-13 peptide

<400> SEQUENCE: 26

Lys Arg Gly Ile Val Glu Gln Cys Cys Thr Ser Ile Ser Ser Leu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic mouse S-13 peptide

<400> SEQUENCE: 27
```

```
Lys Arg Gly Ile Val Asp Gln Cys Cys Thr Ser Ile Cys Ser Leu
1               5                   10                  15
```

<210> SEQ ID NO 28
<211> LENGTH: 26
<212> TYPE: DNA
<213> ORGANISM: Artificial Sequence
<220> FEATURE:
<223> OTHER INFORMATION: Forward anchor prime for cloning TCR

<400> SEQUENCE: 28
cactcgagcg gccccccccc cccccc                                          26

<210> SEQ ID NO 29
<211> LENGTH: 20
<212> TYPE: DNA
<213> ORGANISM: Artificial Sequence
<220> FEATURE:
<223> OTHER INFORMATION: TCR alpha-chain reverse primer

<400> SEQUENCE: 29
cagcaacgtc tctgtctctg                                                 20

<210> SEQ ID NO 30
<211> LENGTH: 36
<212> TYPE: DNA
<213> ORGANISM: Artificial Sequence
<220> FEATURE:
<223> OTHER INFORMATION: TCR beta-chain reverse primer

<400> SEQUENCE: 30
gctctagcgt cgacggctgc tcaggcagta tctgga                               36

<210> SEQ ID NO 31
<211> LENGTH: 20
<212> TYPE: PRT
<213> ORGANISM: Artificial Sequence
<220> FEATURE:
<223> OTHER INFORMATION: Synthetic peptide for mouse proinsulin II amino
      acids C53-A7

<400> SEQUENCE: 31

```
Leu Gln Thr Leu Ala Leu Glu Val Ala Gln Gln Lys Arg Gly Ile Val
1               5                   10                  15

Asp Gln Cys Cys
            20
```

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide for mouse II amino acids
      C64-A13

<400> SEQUENCE: 32

```
Lys Arg Gly Ile Val Asp Gln Cys Cys Thr Ser Ile Cys Ser Leu
1               5                   10                  15
```

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide for mouse proinsulin II amino
      acids C64-A13

<400> SEQUENCE: 33

```
Lys Arg Gly Ile Val Asp Gln Ser Ser Thr Ser Ile Ser Ser Leu
1               5                   10                  15

<210> SEQ ID NO 34
<211> LENGTH: 13
<212> TYPE: PRT
<213> ORGANISM: Homo sapiens

<400> SEQUENCE: 34

Gly Ile Val Glu Gln Cys Cys Thr Ser Ile Cys Ser Leu
1               5                   10

<210> SEQ ID NO 35
<211> LENGTH: 13
<212> TYPE: PRT
<213> ORGANISM: Mus musculus

<400> SEQUENCE: 35

Gly Ile Val Asp Gln Cys Cys Thr Ser Ile Cys Ser Leu
1               5                   10

<210> SEQ ID NO 36
<211> LENGTH: 15
<212> TYPE: PRT
<213> ORGANISM: Homo sapiens

<400> SEQUENCE: 36

Phe Val Asn Gln His Leu Ala Gly Ser His Leu Val Glu Ala Leu
1               5                   10                  15

<210> SEQ ID NO 37
<211> LENGTH: 15
<212> TYPE: PRT
<213> ORGANISM: Homo sapiens

<400> SEQUENCE: 37

His Leu Ala Gly Ser His Leu Val Glu Ala Leu Tyr Leu Val Ala
1               5                   10                  15

<210> SEQ ID NO 38
<211> LENGTH: 15
<212> TYPE: PRT
<213> ORGANISM: Homo sapiens

<400> SEQUENCE: 38

Ser His Leu Val Glu Ala Leu Tyr Leu Val Ala Gly Glu Arg Gly
1               5                   10                  15

<210> SEQ ID NO 39
<211> LENGTH: 15
<212> TYPE: PRT
<213> ORGANISM: Homo sapiens

<400> SEQUENCE: 39

Glu Ala Leu Tyr Leu Val Ala Gly Glu Arg Gly Phe Phe Tyr Thr
1               5                   10                  15

<210> SEQ ID NO 40
<211> LENGTH: 15
<212> TYPE: PRT
<213> ORGANISM: Homo sapiens

<400> SEQUENCE: 40

Leu Val Ala Gly Glu Arg Gly Phe Phe Tyr Thr Pro Lys Thr Arg
1               5                   10                  15
```

<210> SEQ ID NO 41
<211> LENGTH: 15
<212> TYPE: PRT
<213> ORGANISM: Homo sapiens

<400> SEQUENCE: 41

Glu Arg Gly Phe Phe Tyr Thr Pro Lys Thr Arg Arg Glu Ala Glu
1               5                   10                  15

<210> SEQ ID NO 42
<211> LENGTH: 15
<212> TYPE: PRT
<213> ORGANISM: Homo sapiens

<400> SEQUENCE: 42

Phe Tyr Thr Pro Lys Thr Arg Arg Glu Ala Glu Asp Leu Gln Val
1               5                   10                  15

<210> SEQ ID NO 43
<211> LENGTH: 15
<212> TYPE: PRT
<213> ORGANISM: Homo sapiens

<400> SEQUENCE: 43

Lys Thr Arg Arg Glu Ala Glu Asp Leu Gln Val Gly Gln Val Glu
1               5                   10                  15

<210> SEQ ID NO 44
<211> LENGTH: 15
<212> TYPE: PRT
<213> ORGANISM: Homo sapiens

<400> SEQUENCE: 44

Glu Ala Glu Asp Leu Gln Val Gly Gln Val Glu Leu Gly Gly Gly
1               5                   10                  15

<210> SEQ ID NO 45
<211> LENGTH: 15
<212> TYPE: PRT
<213> ORGANISM: Homo sapiens

<400> SEQUENCE: 45

Leu Gln Val Gly Gln Val Glu Leu Gly Gly Gly Pro Gly Ala Gly
1               5                   10                  15

<210> SEQ ID NO 46
<211> LENGTH: 15
<212> TYPE: PRT
<213> ORGANISM: Homo sapiens

<400> SEQUENCE: 46

Gln Val Glu Leu Gly Gly Gly Pro Gly Ala Gly Ser Leu Gln Pro
1               5                   10                  15

<210> SEQ ID NO 47
<211> LENGTH: 15
<212> TYPE: PRT
<213> ORGANISM: Homo sapiens

<400> SEQUENCE: 47

Gly Gly Gly Pro Gly Ala Gly Ser Leu Gln Pro Leu Ala Leu Glu
1               5                   10                  15

<210> SEQ ID NO 48

-continued

```
<211> LENGTH: 15
<212> TYPE: PRT
<213> ORGANISM: Homo sapiens

<400> SEQUENCE: 48

Gly Ala Gly Ser Leu Gln Pro Leu Ala Leu Glu Gly Ser Leu Gln
1               5                   10                  15

<210> SEQ ID NO 49
<211> LENGTH: 15
<212> TYPE: PRT
<213> ORGANISM: Homo sapiens

<400> SEQUENCE: 49

Leu Gln Pro Leu Ala Leu Glu Gly Ser Leu Gln Lys Arg Gly Ile
1               5                   10                  15

<210> SEQ ID NO 50
<211> LENGTH: 15
<212> TYPE: PRT
<213> ORGANISM: Homo sapiens

<400> SEQUENCE: 50

Ala Leu Glu Gly Ser Leu Gln Lys Arg Gly Ile Val Glu Gln Ala
1               5                   10                  15

<210> SEQ ID NO 51
<211> LENGTH: 15
<212> TYPE: PRT
<213> ORGANISM: Homo sapiens

<400> SEQUENCE: 51

Ser Leu Gln Lys Arg Gly Ile Val Glu Gln Ala Ala Thr Ser Ile
1               5                   10                  15

<210> SEQ ID NO 52
<211> LENGTH: 15
<212> TYPE: PRT
<213> ORGANISM: Homo sapiens

<400> SEQUENCE: 52

Arg Gly Ile Val Glu Gln Ala Ala Thr Ser Ile Ala Ser Leu Tyr
1               5                   10                  15

<210> SEQ ID NO 53
<211> LENGTH: 15
<212> TYPE: PRT
<213> ORGANISM: Homo sapiens

<400> SEQUENCE: 53

Glu Gln Ala Ala Thr Ser Ile Ala Ser Leu Tyr Gln Leu Glu Asn
1               5                   10                  15

<210> SEQ ID NO 54
<211> LENGTH: 14
<212> TYPE: PRT
<213> ORGANISM: Homo sapiens

<400> SEQUENCE: 54

Thr Ser Ile Ala Ser Leu Tyr Gln Leu Glu Asn Tyr Ala Asn
1               5                   10

<210> SEQ ID NO 55
<211> LENGTH: 14
<212> TYPE: PRT
<213> ORGANISM: Mus musculus
```

```
<400> SEQUENCE: 55

Arg Gly Ile Val Glu Gln Ala Ala Thr Ser Ile Ala Ser Leu
1               5                   10

<210> SEQ ID NO 56
<211> LENGTH: 17
<212> TYPE: PRT
<213> ORGANISM: Homo sapiens

<400> SEQUENCE: 56

Cys Ala Asp Ser Arg Ala Phe Ser Gly Gly Tyr Asn Lys Leu Ile Phe
1               5                   10                  15

Gly

<210> SEQ ID NO 57
<211> LENGTH: 17
<212> TYPE: PRT
<213> ORGANISM: Homo sapiens

<400> SEQUENCE: 57

Cys Ala Ala Pro Ile Leu Phe Ser Gly Gly Tyr Asn Lys Leu Ile Phe
1               5                   10                  15

Gly

<210> SEQ ID NO 58
<211> LENGTH: 17
<212> TYPE: PRT
<213> ORGANISM: Homo sapiens

<400> SEQUENCE: 58

Cys Ala Asp Ser Arg Ala Phe Ser Gly Gly Tyr Asn Lys Leu Ile Phe
1               5                   10                  15

Gly

<210> SEQ ID NO 59
<211> LENGTH: 17
<212> TYPE: PRT
<213> ORGANISM: Homo sapiens

<400> SEQUENCE: 59

Cys Ala Asp Ser Arg Ala Phe Ser Gly Gly Tyr Asn Lys Leu Ile Phe
1               5                   10                  15

Gly

<210> SEQ ID NO 60
<211> LENGTH: 16
<212> TYPE: PRT
<213> ORGANISM: Homo sapiens

<400> SEQUENCE: 60

Cys Ala Ser Ser Leu Tyr Pro Gly Asp Leu Pro Glu Ala Phe Phe Gly
1               5                   10                  15

<210> SEQ ID NO 61
<211> LENGTH: 15
<212> TYPE: PRT
<213> ORGANISM: Homo sapiens

<400> SEQUENCE: 61

Cys Ala Ser Ser Leu Ile Gly Ser Ala Thr Glu Ala Phe Phe Gly
1               5                   10                  15
```

```
<210> SEQ ID NO 62
<211> LENGTH: 16
<212> TYPE: PRT
<213> ORGANISM: Homo sapiens

<400> SEQUENCE: 62

Cys Ala Ser Ser Leu Tyr Pro Gly Asp Leu Pro Glu Ala Phe Phe Gly
1               5                   10                  15

<210> SEQ ID NO 63
<211> LENGTH: 16
<212> TYPE: PRT
<213> ORGANISM: Homo sapiens

<400> SEQUENCE: 63

Cys Ala Ser Ser Leu Tyr Pro Gly Asp Leu Pro Glu Ala Phe Phe Gly
1               5                   10                  15

<210> SEQ ID NO 64
<211> LENGTH: 15
<212> TYPE: PRT
<213> ORGANISM: Homo sapiens

<400> SEQUENCE: 64

Lys Arg Gly Ile Val Glu Gln Cys Cys Thr Ser Ile Cys Ser Leu
1               5                   10                  15

<210> SEQ ID NO 65
<211> LENGTH: 15
<212> TYPE: PRT
<213> ORGANISM: Homo sapiens

<400> SEQUENCE: 65

Gln Cys Cys Thr Ser Ile Cys Ser Leu Tyr Gln Leu Glu Asn Tyr
1               5                   10                  15
```